US007501133B2

(12) United States Patent
McNally-Heintzelman et al.

(10) Patent No.: US 7,501,133 B2
(45) Date of Patent: Mar. 10, 2009

(54) LIGHT-ACTIVATED ADHESIVE COMPOSITE, SYSTEM, AND METHODS OF USE THEREOF

(75) Inventors: Karen M. McNally-Heintzelman, Cambridge, MA (US); Douglas L. Heintzelman, Cambridge, MA (US); Jeffrey N. Bloom, Chicago, IL (US); Mark T. Duffy, Chicago, IL (US)

(73) Assignees: Rose-Hulman Institute of Technology, Terre Haute, IN (US); The Board of Trustees of the University of Illinois, Urbana, IL (US)

( * ) Notice: Subject to any disclaimer, the term of this patent is extended or adjusted under 35 U.S.C. 154(b) by 634 days.

(21) Appl. No.: 10/757,818

(22) Filed: Jan. 15, 2004

(65) Prior Publication Data
US 2004/0236371 A1 Nov. 25, 2004

Related U.S. Application Data

(63) Continuation-in-part of application No. 10/610,068, filed on Jun. 30, 2003.

(60) Provisional application No. 60/442,644, filed on Jan. 24, 2003.

(51) Int. Cl.
*A61F 13/00* (2006.01)
(52) U.S. Cl. .................. 424/422; 424/444; 424/400
(58) Field of Classification Search .................. None
See application file for complete search history.

(56) References Cited

U.S. PATENT DOCUMENTS

| 4,841,962 | A | 6/1989 | Berg et al. |
| 5,292,362 | A | 3/1994 | Bass et al. |
| 6,258,872 | B1 | 7/2001 | Stedronsky |
| 6,340,495 | B1 | 1/2002 | Sumian et al. |
| 6,391,049 | B1 | 5/2002 | McNally et al. |

FOREIGN PATENT DOCUMENTS

| WO | WO 92/13495 | 8/1992 |
| WO | WO 00/74742 | 12/2000 |
| WO | WO 01/28600 | 4/2001 |
| WO | WO 01/89431 | 11/2001 |

OTHER PUBLICATIONS

Byrd et al., "Absorption properties of alternative chromophores for use in laser tissue soldering applications", 2003.*
Davis et al., Optimization of Laser-solder repair technique for possible application in strabismus surgeries, Biomed Sci Instrum 2002, 351—356.*
Soller et al., Use of Infrared temperature monitering system to determine optimal temperature for laser-solder tissue repair, Biomed Sci Instrum 2002 339—344.*
Hoffman et al., Biodegradable synthetic polymer scaffolds for reinforcement of albumin protein solders used for laser assisted tissue repari Biomed Sci Instrum 2002, 339—344.*
Brooks et al., Exogenous chromophore for the argon and Nd:YAG lasers: a potential application to laser tissue interations Lasers in Surgery and Medince 1992, 294—302.*
Birch et al., Methylene blue based protein solder for vascular anastomes: an in vitro burst pressure study Lasers in Surgery and Medicine 2000, 323-329.*
Wang et al., New Technique for Laryngotracheal mucosa transplataion Arch Otolaryngol Head Neck Surg/ vol. 121 Jul. 1995 773—777.*
Wadia et al., Sutureless liver repair and hemorrhage control using laser-mediated fusion of human albumin as solder, J. Trauma. 2001 51—59.*
McNally et al., Photothermal effects of laser tissue soldering, Phys Med Biol 1999 983—1002.*
McNally et al., Novel solid protein solder designs for laser-assisted tissue repair, Lasers in Surgery and Medicine, 2000, 147—157.*
Sorg et al., Laser-tissue soldering with biodegradable polymer films in vitro: film surface morphology and hydration effects, Lasers in Surgery and Medicine 2001, 297-306.*
Poppas et al., Patch Graft Urethroplasty using dye enhanced laser tissue welding with a human protein solder: a preclinical canine model, J Urology 1993, 648-650.*
Xie et al., Laser welding with an albumin stent: experimental ureteral end to end anastomosis, Lasers in Surgery, 2000, 215—220.*
Riley et al., Biomed Sci Instrum (37) 451—456, 2001.*
McNally et al in Journal of Biomedical Optics 6(11) 68—73, Jan. 2001.*
By Moser et al. "New Range of Light-Activated Surgical Adhesives for Tissue Repair", Biomed Sci Instru, 37, 441-449, 2001.*
Hoffman et al., Biomed Sci Instrum 2003; 39:12-17, 2003.*
Pitts et al., in Photochemistry and Photobiology, 2002, 76(2): 135-144.*
Riley et al., "Application of a New Range of Light-Activated Surgical Adhesives for Vascular Repair in a Canine Model," *Journal of Cardiovascular Medicine & Science*, vol. 3, Nos. 3-4, pp. 135-138, 2000.
McNally-Heintzelman et al., "In vivo Tissue Repair using Light-Activated Surgical Adhesive in a Porcine Model," *Proc. SPIE*, vol. 4244 pp. 226-232, 2001.
McNally-Heintzelman et al., "Improved Vascular Tissue Fusion Using New Light Activated Surgical Adhesives in a Canine Model," *J. Biomed. Opt.*, vol. 6, No. 1, pp. 68-73, 2001.
Wake et al., "Fabrication of Pliable Biodegradable Polymer Foams to Engineer Soft Tissue," *Cell Transplant.*, vol. 5, No. 4, pp. 465-473, 1996.
Taravella et al., "2-Octyl Cyanoacrylate Medical Adhesive in Treatment of a Corneal Perforation," *Cornea*, vol. 20, No. 2, pp. 220-221, 2001.
Spierer et al., "Reattachment of Extraocular Muscles Using Fibrin Glue in a Rabbit Model," *Invest. Ophthalmol. Vis. Sci.*, vol. 38, pp. 543-546, 1997.

(Continued)

*Primary Examiner*—Michael G Hartley
*Assistant Examiner*—Eric E Silverman
(74) *Attorney, Agent, or Firm*—Bose McKinney & Evans LLP

(57) ABSTRACT

The present invention provides a light-activated adhesive composite suitable for medical and surgical applications. The composite includes a scaffold and a light-activated adhesive, such as a laser tissue solder. The scaffold includes a biological, biocompatible, or biodegradable material, such as PLGA or SIS.

26 Claims, 19 Drawing Sheets
(4 of 19 Drawing Sheet(s) Filed in Color)

OTHER PUBLICATIONS

Ricci et al., "Octyl 2-Cyanoacrylate in Sutureless Surgery of Extraocular Muscles: An Experimental Study on the Rabbit Model," *Graefe's Arch. Clin. Exp. Ophthalmol.*, vol. 238, pp. 454-458, 2000.

Quinn et al., "A Randomized Trial Comparing Octyleyanoacrylate Tissue Adhesive and Sutures in the Management of Lacerations," *JAMA*, vol. 277. pp. 1527-1530, 1997.

Trott, "Cyanoacrylate Tissue Adhesives. An Advance in Wound Care," *JAMA*, vol. 277, pp. 1559-1560, 1997.

Detweiler et al., "Sutureless and Reduced Suture Anastomosis of Hollow Vessels with Fibrin Glue: A Review," *J. Invest. Surg.*, vol. 12, pp. 245-262, 1999.

Shah et al., "Fibrin Glue Fixation of a Digital Osteochondral Fracture: Case Report and Review of the Literature," *J. Hand Surg. (Am).*, vol. 27, pp. 464-469, 2002.

Reed et al., Biodegradable Polymers for Use in Surgery-Poly(glycolic(/Poly(lactic acid) Homo and Copolymers: 2, *In Vitro Degradation Polymer*, vol. 22, pp. 499-504, 1981.

Riley et al., "Improved Laser Assisted Vascular Tissue Fusion using Light-Activated Surgical Adhesive in a Porcine Model," *Biomed. Sci. Instrum.*, vol. 37, pp. 451-456, 2001.

Jain et al., "Repair of Small Blood Vessels with the Neodymium-YAG Laser: A Preliminary Report," *Surgery*, vol. 85, No. 6, pp. 684-688, 1979.

Krueger et al., "Argon Laser Coagulation of Blood for the Anastomosis of Small Vessels," *Lasers Surg. Med.*, vol. 5, No. 1, pp. 55-60, 1985.

Poppas et al., "Laser Welding in Urethral Surgery: Improved Results with a Protein Solder," *J. of Urology*, vol. 139, No. 2, pp. 415-417, 1988.

Oz et al., "Tissue Soldering by Use of Indocyanine Green Dye-Enhanced Fibrinogen with the Near Infrared Diode Laser," *J. Vasc. Surg.*, vol. 11, pp. 718-725, 1990.

Kirsch et al., "Laser Tissue Soldering for Hypospadias Repair: Results of a Controlled Prospective Clinical Trial," *J. Urol.*, vol. 165, No. 2, pp. 574-577, 2001.

Wright et al., "Effect of Laser Wavelength and Protein Solder Concentration on Acute Tissue Repair Using Laser Welding: Initial Results in a Canine Ureter Model," *Tech. Urol.*, vol. 3, No. 3, pp. 176-181, 1997.

McNally et al., "Optimal Parameters for Laser Tissue Soldering. Part I: Tensile Strength and Scanning Electron Microscopy Analysis," *Lasers Surg. Med.*, vol. 24, No. 5, pp. 319-331, 1999.

McNally et al., "Novel Solid Protein Solder Designs for Laser-Assisted Tissue Repair," *Lasers Surg. Med.*, vol. 27, No. 2, pp. 147-157, 2000.

Mulroy et al., "Photochemical Keratodesmos for Repair of Lamellar Corneal Incisions," *Invest. Ophthalmol. Vis. Sci.*, vol. 41, No. 11, pp. 3335-3340, 2000.

Fried et al., "Laser Skin Welding: In Vivo Tensile Strength and Wound Healing Results," *Lasers Surg. Med.*, vol. 27, No. 1, pp. 55-65, 2000.

Mikos et al., "Preparation and Characterizaiton of Poly(L-Lactic Acid) Foams," *J. Biomed. Mat. Res.*, vol. 27, No. 2, pp. 183-189, 1993.

McNally et al., "Optical-Thermal Characterization of Albumin Protein Solders," *App. Opt.*, vol. 38, No. 31, pp. 6661-6672, 1999.

McNally et al., "Photothermal Effects of Laser Tissue Soldering," *Phys. Med. Biol.*, vol. 44, pp. 983-1002, 1999.

Arakawa et al., "Analysis of the Heat-Induced Denaturation of Proteins using Temperature Gradient Gel Electrophoresis," *Anal. Biochem.*, vol. 208, No. 2, pp. 255-259, 1993.

Pico, "Thermodynamic Aspects of the Thermal Stability of Human Serum Albumin," *Biochem. Mol. Biol. Int.*, vol. 36, No. 5, pp. 1017-1023, 1995.

Brooks et al., "Exogenous Chromophores for the Argon and Nd:YAG Lasers: A Potential Application to Laser-Tissue Interactions," *Lasers. Surg. Med.*, vol. 12, No. 3, pp. 294-302, 1992.

Oz et al., "In Vitro Comparison of Thulium-Holmium-Chromium: YAG and Argon Ion Lasers for Welding Biliary Tissue," *Lasers. Surg. Med.*, vol. 9, No. 3, pp. 248-253, 1989.

Poppas et al., "Chromophore Enhanced Laser Welding of Canine Ureters in Vitro Using a Human Protein Solder: A Preliminary Step for Laparoscopic Tissue Welding," *J. Urol.*, vol. 150, pp. 1050-1055, 1993.

Self et al., "Limited Thrombogenicity of Low Temperature, Laser-Welded Vascular Anastomoses," *Lasers. Surg. Med.*, vol. 18, No. 3, pp. 241-247, 1996.

Poppas et al., "Human Albumin Solders for Clinical Application During Laser Tissue Welding," *Lasers. Surg. Med.*, vol. 19, No. 1, pp. 2-8, 1996.

Khadem et al., "Photodynamic Tissue Adhesion with Chlorin(e6) Protein Conjugates," *Invest. Ophthalmol. Vis. Sci.*, vol. 40, No. 13, pp. 3132-3137, 1999.

Poppas et al., "Human Albumin Solder Supplemented with TGF-$\beta$1 Accelerates Healing Following Laser Welded Wound Closure," *Lasers Surg. Med.*, vol. 19, No. 3, pp. 360-368, 1996.

Lauto et al., "Laser-Activated Solid Protein Bands for Peripheral Nerve Repair: An In Vivo Study," *Lasers Surg. Med.*, vol. 21, No. 2, pp. 134-141, 1997.

Bass et al., "Laser Tissue Welding: A Comprehensive Review of Current and Future Clinical Applications," *Lasers Surg. Med.*, vol. 17, No. 4, pp. 315-349, 1995.

Oz et al., "Comparison of Laser-Assisted Fibrinogen-Bonded and Sutured Canine Arteriovenous Anastomoses," *Surgery*, vol. 112, pp. 76-83, 1992.

Maitz et al., "Sutureless Microvascular Anastomoses by a Biodegradable Laser-Activated Solid Protein Solder," *Plast. Reconstr. Surg.*, vol. 104, No. 6, pp. 1726-1731, 1999.

Lauto et al., "Carotid Artery Anastomosis with Albumia Solder and Near Infrared Lasers: A Comparative Study," *Lasers Surg. Med.*, vol. 28, No. 1, pp. 50-55, 2001.

Kirsch et al., "Laser Soldering Technique for Sutureless Urethral Surgery," *Tech. Urol.*, vol. 3, No. 2, pp. 108-113, 1997.

Trickett et al., "Laser Welding of Vas Deferens in Rodents: Initial Experience with Fluid Solders," *Microsurgery*, vol. 18, No. 7, pp. 414-418, 1998.

Kirsch et al., "Laser Soldering Technique for Sutureless Urethral Surgery," *Tech. Urol.*, vol. 3, No. 2, pp. 108-113, 1997.

Barrieras et al., "Lessons Learned from Laser Tissue Soldering and Fibrin Glue Pyeloplasty in an In Vivo Porcine Model," *J. Urol.*, vol. 164, No. 3, part 2, pp. 1106-1110, 2000.

Wadia et al., "Sutureless Liver Repair and Hemorrhage Control using Laser-Mediated Fusion of Human Albumin as a Solder," *J. Trauma*, vol. 51, No. 1, pp. 51-59, 2001.

Lauto et al., "Laser Nerve Repair by Solid Protein Band Technique II: Assessment of Long-Term Nerve Regeneration," *Microsurgery*, vol. 18, No. 1, pp. 60-64, 1998.

Foyt et al., "Dural Closure with Laser Tissue Welding," *Otolaryngol. Head Neck Surg.*, vol. 115, No. 6, pp. 513-518, 1996.

Kirsch et al., "Laser Welding with Albumin-Based Solder: Experimental Full-Tubed Skin Graft Urethroplasty," *Lasers Surg. Med.*, vol. 18, No. 3, pp. 225-230, 1996.

Suh et al., "Comparison of Dermal and Epithelial Approaches to Laser Tissue Soldering for Skin Flap Closure," *Lasers Surg. Med.*, vol. 22, No. 5, pp. 268-274, 1998.

Cooper et al., "Optimal Solder and Power Density for Diode Laser Tissue Soldering (LTS)," *Lasers Surg. Med.*, vol. 29, No. 1, pp. 53-61, 2001.

Wang et al., "New Technique for Laryngotracheal Mucosa Transplantation 'Stamp' Welding using Indocyanine Green Dye and Albumin Interaction with Diode Laser," *Arch. Otolaryngol. Head. Neck Surg.*, vol. 121, No. 7, pp. 773-777, 1995.

Zuger et al., "Laser Soldering Welding of Articular Cartilage: Tensile Strength and Chondrocyte Viability," *Lasers Surg. Med.*, vol. 28, No. 5, pp. 427-434, 2001.

Mikos et al., "Formation of Highly Porous Biodegradable Scaffolds for Tissue Engineering," *Electronic J. Biotech.* [online]. Aug. 15, 2000, vol. 3, No. 2 [cited Dec. 15, 2003]. Available from http://www.eibiotechnology.info/content/vol13/issue2/full/5/index.html. ISSN 0717-3458.

Butler et al., "Absorption of Serum Albumin to Thin Films of Poly (lactide-do-glycolide)," *J. Control. Release*, vol. 58, No. 3, pp. 335-347, 1999.

Simon et al., "Long-Term Appearance of Lacerations Repaired using a Tissue Adhesive," *Pediatrics*, vol. 99, No. 2, pp. 193-195, 1997.

Bruns et al., "Laceration Repair using a Tissue Adhesive in a Children's Emergency Department," *Pediatrics*, vol. 98, No. 4, part 1, pp. 673-675, 1996.

Maluf-Filho et al., "Endoscopic Sclerosis Versus Cyanoacrylate Endoscopic Injection for the First Episode of Variceal Bleeding: A Prospective, Controlled. and Randomized Study in Child-Pugh Class C Patients," *Endoscopy.*, vol. 33, No. 5, pp. 421-427, 2001.

Hallock et al., "Expanded Applications for Octyl-2-Cyanoacrylate as a Tissue Adhesive," *Ann. Plast. Surg.*, vol. 46, No. 2, pp. 185-189, 2001.

Zafar et al., "Sutureless Circumcision," *Br. J. Surg.*, vol. 80, No. 7, p. 859, 1993.

Lapointe et al., "Early Closure of Fistula After Hypospadias Surgery using N-Butyl Cyanoacrylate: Preliminary Results," *J. Urol.*, vol. 168, No. 4, part 2, pp. 1751-1753, 2002.

Ferlise et al., "Use of Cyanoacrylate Tissue Adhesive under a Diaper," *BJU Int.*, vol. 87, No. 7, pp. 672-673, 2001.

Rosin et al., "Closure of Laparoscopic Trocar Site Wounds with Cyanoacrylate Tissue Glue: A Simple Technical Solution," *J. Laparoendosc. Adv. Surg. Tech. A.*, vol. 11, No. 3, pp. 157-159, 2001.

Frye, "Can We Really Use Super Glue Instead of Suture?," *Midwifery Today Childbirth Educ.*, vol. 38, pp. 13-14, 1996.

McNally et al., "ICG-Doped Albumin Protein Solders for Improved Tissue Repair," *Proc. SPIE*, vol. 3590, pp. 99-110, 1999.

Sauda et al., "Determination of Protein in Human Serum by High Performance Liquid Chromatography," *Anal. Chem.*, vol. 58, pp. 2649-2653. 1986.

Kijsamanmith et al., "Micro-tensile Bond Strengths of Bonding Agents to Pupal Floor Dentine." *International Endodontic Journal*, vol. 35, pp. 833-839, 2002.

Kamer et al., "Histoacryl: Its Use in Aesthetic Facial Plastic Surgery," *Arch. Otolaryngol. Head Neck Surg.*, vol. 115, pp. 193-197, 1989.

Noel et al., "Retinal Perforation in Strabismus Surgery," *Journal Pediatr. Ophthalmol. Strabismus*, vol. 34, pp. 115-117, 1997.

Awad et al., "Recognized Globe Perforation During Strabismus Surgery; Incidence, Risk Factors, and Sequelae," *JAAPOS*, vol. 4, pp. 150-153. 2000.

Recchia et al., "Endophthalmitis After Pediatric Strabismus Surgery," *Ophthalmol.*, vol. 118, pp. 939-944, 2000.

Whitson et al., "Penetrating Keratoplasty and Keratoprosthesis," Tasman W., Jaeger, EA (ed.); *Duane's Clinical Ophthalmology*, Philadelphia, Lippincott Williams and Wilkins; vol. 6, chap. 26, pp. 1-28, 2001.

Vote et al., "Cyanoacrylate Glue for Corneal Perforations: A Description of a Surgical Technique and a Review of the Literature," *Clin. Experiment Ophthalmol.*, vol. 28, pp. 437-442, 2000.

Gupta et al., "2-Octyl Cyanoacrylate Tissue Adhesive and Muscle Attachment to Porous Anophthalmic Orbital Implants," *Ophthal. Plast. Reconstr. Surg.*, vol. 17, pp. 264-269, 2001.

Burnstein et al., "Conjunctival Advancement Versus Nonincisional Treatment for Late-Onset Glaucoma Filtering Bleb Leaks," *Ophthalmology*, vol. 109, pp. 71-75, 2002.

Menovsky et al., "Laser Tissue Welding of Dura Mater and Peripheral Nerves: A Scanning Electron Microscopy Study," *Lasers Surg. Med.*, vol. 19, pp. 152-158, 1996.

Currie et al., "The Use of Fibrin Glue in Skin Grafts and Tissue-Engineered Skin Replacements: A Review," *Plast. Reconstr. Surg.*, vol. 108, pp. 1713-1726, 2001.

Holland et al., "Polymers for Biodegradable Medical Devices. I. The Potential of Polyesters as Controlled Macromolecular Release Systems," *J. Controlled Release*, vol. 4, pp. 155-180, 1986.

Collins et al., "Extraocular Muscle Forces in Normal Human Subjects," *Invest. Ophthalmol. Vis. Sci.*, vol. 20, pp. 652-664, 1981.

Zieren et al., "Effects of Fibrin Glue and Growth Factors Released from Platelets on Abdominal Hernia Repair with a Resorbable PGA Mesh; Experimental Study," *J. Surg. Res.*, vol. 85, pp. 267-272, 1999.

Auteri et al., "Diode Laser Tracheal Anastomosis (Abstract)," *Journal of Investigative Surgery*, vol. 3, p. 301, 1990.

Latta et al., "Bond Strength of a Resin Cement to a Cured Composite Inlay Material," *J. Prosthet. Dent.*, vol. 72, pp. 189-193, 1994.

Birch et al., "Methylene Blue Based Protein Solder for Vascular Anastomoses: An in Vitro Burst Pressure Study," *Lasers Surg. Med.*, vol. 26, No. 3, pp. 323-329, 2000.

Small et al., "Experimental and Computational Laser Welding using a Protein Patch," *J. Biomed. Opt.*, vol. 3, No. 1, pp. 96-101, 1998.

La Joie et al., "Welding Artificial Biomaterial with a Pulsed Diode Laser and Indocyanine Green Dye," *Proc. SPIE*, vol. 2395, pp. 508-516, 1995.

Xie et al., "Laser Welding With an Albumin Stent: Experimental Ureteral End-to-End Anastomosis," *Proc. SPIE*, vol. 3907, pp. 215-220, 2000.

Kokosa et al., "Laser-Initiated Decomposition Products of Indocyanine Green (ICG) and Carbon Black Sensitized Biological Tissues," *Proc. SPIE*, vol. 2974, pp. 205-213, 1997.

Glinsky et al., "Modeling of Endovascular Patch Welding Using the Computer Program LATIS," *Proc. SPIE*, vol. 2623, pp. 349-358, 1995.

Landsman et al., "Light-Absorbing Properties, Stability, and Spectral Stabilization of Indocyanine Green," *J. Appl. Physiol.*, vol. 40, No. 4, pp. 575-583, 1976.

Zhou et al, "Aggregation and Degradation of Indocyanine Green," *Proc. SPIE*, vol. 2128, pp. 495-505, 1994.

Dimitrov et al., "Thermal Breakdown Properties of Indocyanine Green," *Proc. SPIE*, vol. 2395, pp. 486-489, 1995.

Gathje et al., "Stability Studies on Indocyanine Green Dye," *J. Appl. Physiol.*, vol. 29, pp. 181-185, 1970.

Beat et al., "Laser Balloon Vascular Welding using a Dye-Enhanced Albumin Solder," *Proc. SPIE*, vol. 4244, pp. 183-197, 2001.

Kirsch et al., "Hypospadias Repair using Laser Tissue Soldering (LTS): Preliminary Results of a Prospective Randomized Study," *Proc. SPIE*, vol. 3245, pp. 309-312, 1998.

Xie et al., "Thermal Damage Control of Dye-Assisted Laser Tissue Welding: Effect of Dye Concentration," *Proc. SPIE*, vol. 4244, pp. 189-192, 2001.

Bass et al., "Feasibility Studies for Laser Solder Neurorrhaphy," *Proc. SPIE*, vol. 2128, pp. 472-475, 1994.

Liu et al., "Embolizatin of Cerebral Arteriovenous Malformations with n-butyl-2-Cyanoacrylate," *J. Formas. Med. Assoc.*, vol. 99, No. 12, pp. 906-713, 2000.

Adoni et al., "The use of Histoacryl for Episiotomy Repair," *Br. J. Obstet. Gynaecol.*, vol. 98, No. 5, pp. 476-478, 1991.

Ong et al., "Comparing Wound Closure Using Tissue Glue Versus Subcuticular Suture for Pediatric Surgical Incisions: A Prospective, Randomized Trial," *Pediatr. Surg. Int.*, vol. 18, Nos. 5-6, pp. 553-555, 2002.

Erbil et al., "An Experimental Study on the Use of Fibrin Sealants in Strabismus Surgery," *Turk J. Pediatric.*, vol. 33, pp. 111-116, 1991.

McNally-Heintzelman et al., "Chapter 39: Laser Tissue Welding," in Vo-Dinh T (ed.), *Biomedical Photonics Handbook*; Boca Raton; CRC Press, (to be published Dec. 2002), pp. 1-45; Color Figures 1.1-62.2.

* cited by examiner

LIGHT-ACTIVATED ADHESIVE COMPOSITE, SYSTEM, AND METHODS OF USE THEREOF

RELATED APPLICATIONS

This application is a continuation-in-part of U.S. patent application Ser. No. 10/610,068, filed Jun. 30, 2003. This application also claims the benefit of U.S. Provisional Patent Application No. 60/442,644, filed Jan. 24, 2003, which is incorporated herein by this reference.

TECHNICAL FIELD

The present invention relates to the field of biological tissue repair and/or wound closure, e.g., after injury to the tissue or surgery. More particularly, the present invention relates to the use of light-activated biological or biocompatible adhesive composites for the repair of biological tissue.

BACKGROUND

Known methods of biological tissue repair include sutures, staples and clips, sealants, and adhesives. Sutures are inexpensive, reliable, readily available and can be used on many types of lacerations and incisions. However, the use of sutures has many drawbacks. Sutures are intrusive in that they require puncturing of the tissue. Also, sutures require technical skill for their application. Sutures must be placed very precisely in order to properly align the tissue. Often the tissue must be manually realigned before each pass of the suture's needle. Imprecise placement of a suture may necessitate its removal and replacement; as a result, delicate tissues may be damaged. Sutures frequently must be removed postoperatively. Not only is this also time-consuming, but children often require either restraint, sedation, or additional exposure to general anesthetics. Sutures can also produce foreign body reactions and act as a nidus for infection. Finally, sutures pose the risk of needle-stick injury and transmissible infections for operating room personnel.

Staples or clips are preferred over sutures, for example, in minimally invasive endoscopic applications. Staples and clips require less time to apply than sutures, are available in different materials to suit different applications, and generally achieve uniform results. However, staples and clips are not easily adapted to different tissue dimensions and maintaining precision of alignment of the tissue is difficult because of the relatively large force required for application. Further, none of these fasteners is capable of producing a watertight seal for the repair.

Sealants, including fibrin-, collagen-, synthetic polymer- and protein-based sealants, act as a physical barrier to fluid and air, and can be used to promote wound healing, tissue regeneration and clot formation. However, sealants are generally time-consuming to prepare and apply. Also, with fibrin-based sealants, there is a risk of blood-borne viral disease transmission. Further, sealants cannot be used in high-tension areas.

Adhesives, for example, cyanoacrylate glues, have the advantage that they are generally easy to dispense. However, application of adhesives during the procedure can be cumbersome. Because of their liquid nature, these adhesives are difficult to precisely position on tissue and thus require adept and delicate application if precise positioning is desired. Cyanoacrylates also harden rapidly; therefore, the time available to the surgeon for proper tissue alignment is limited. Further, when cyanoacrylates dry, they become brittle. Thus, they cannot be used in areas of the body that have frequent movement. In addition, the currently available adhesives are not optimal for high-tension areas.

Laser tissue solders are a possible alternative for overcoming the problems associated with the above-mentioned techniques. Laser tissue soldering is a bonding technique in which a protein solder is applied to the surface of the tissue(s) to be joined and laser energy is used to bond the solder to the tissue surface(s). The term "light-activated adhesive" as used herein refers to laser tissue solders, as well as other now-known and later-developed adhesives which are used in combination with light energy.

The use of biodegradable polymer scaffolding in laser-solder tissue repairs has been shown to improve the success rate and consistency of such repairs. See, for example, McNally et al., U.S. Pat. No. 6,391,049. Laser-soldering techniques require light energy to be supplied to the repair site to activate the adhesive. Current laser soldering techniques are only suitable for a limited number of clinical applications. Accordingly, there is a need for improvements to currently-known light-activated techniques.

SUMMARY

Novel improvements to biocompatible or biological adhesive composites that result from the combination of a light-activated adhesive and a scaffold material have been invented. The inventors have shown that modifying certain characteristics of the scaffold material, such as surface irregularity, improves the effectiveness of the composite. The new composites have exhibited substantially improved tensile strength and time-to-failure characteristics when compared with sutures and the use of light-activated adhesives alone. The present composites can be used effectively as an adhesive, sealing or repairing device for biological tissue. They may also be used as a depot for drugs in providing medication to a wound or repair site. The composites can be positioned across, on top of, or between two materials to be joined (i.e. tissue-to-tissue or tissue-to-biocompatible implant).

The composites of the present invention are applicable to many fields of surgery, extending from emergency and trauma procedures to elective cosmetic surgery, as well as ophthalmic applications. Examples of external or topical applications for the composite include, but are not limited to, wound closure from trauma or at surgical incision sites.

One aspect of the present invention relates generally to novel combinations of light-activated biological adhesives and light-absorbing compounds that are used for photochemical or photothermal activation of the adhesive. "Light" as used herein includes, but is not limited to, electromagnetic radiation having a wavelength in the visible spectrum or invisible spectrum (e.g., infrared or ultraviolet light). One such combination includes a chromophore such as a readily-available food coloring. Another such combination includes a pharmaceutical that is capable of absorbing photons or electromagnetic radiation at specific wavelengths. Yet another combination includes the use of a pH indicator. Other alternative combinations include water (including water contained within a solder) or hemoglobin as the light absorber.

Another aspect of the present invention relates to novel applications of light-activated biological adhesives. The inventors have shown that certain light-activated adhesive composites of the present invention are effective in a broad range of internal and external surgical or other medical applications, including, but not limited to, certain ophthalmic surgical procedures.

The present invention provides a composition that is suitable for medical and surgical applications. In one embodiment, the composition includes a biologically compatible scaffold material that has at least one irregular surface. The composition also includes a light-activated adhesive such as a protein solder. The light-activated adhesive is coupled to the scaffold to form a composite, such that when the irregular surface of the composite is applied to biological tissue and the composite is activated by light energy to repair the biological tissue, the composite has a tensile strength of at least about 130% of the tensile strength of the adhesive alone.

In another embodiment of the present invention, the time-to-failure of the biological tissue repair is at least about 150% of the time-to-failure of a composite when a smooth surface of the scaffold is applied.

In yet another embodiment, the scaffold surface is modified (e.g., by increasing or decreasing surface irregularity) in order to enhance hemostasis or prevent thrombogenesis.

In an additional embodiment of the present invention, the light-activated adhesive comprises a light absorber. One example of a suitable light absorber is a chromophore. In one embodiment, the light absorber includes one of indocyanine green (ICG), methylene blue (MB), food colorings, pH indicators, water, hemoglobin, and photosensitive pharmaceuticals. In another embodiment of the present invention, the scaffold material is small intestinal submucosa (SIS). In still another embodiment, the scaffold material is poly(L-lactic-co-glycolic acid) (PLGA).

In a further embodiment of the present invention, the composition is adaptable to repair biological tissue. The composition comprises a biologically compatible scaffold material, a light-activated adhesive, and a light absorber including one of food colorings, pH indicators, and photosensitive pharmaceuticals including certain prescription drugs.

In an additional embodiment of the present invention, the light absorber includes one of red food coloring (RFC), blue food coloring (BFC) and green food coloring (GFC). In another embodiment of the present invention, the light absorber is selected to provide a solder/interface temperature of 66±3° C. In yet still another embodiment of the present invention, the light absorber concentration is about 200-1000 µL/13 mL of deionized water. In a further embodiment of the present invention, the light absorber concentration is about 600 µL/13 mL deionized water.

In an additional embodiment of the present invention, the RFC includes red #40 and the BFC includes blue #1. In yet an additional embodiment of the present invention, the GFC includes blue #1 and yellow #5.

In accordance with another embodiment of the present invention, a method for repairing, joining, aligning, or sealing ocular tissues is provided. In one embodiment, the ocular tissue includes at least one of muscle and sclera. The method comprises the steps of combining a biologically compatible scaffold material and a light-activated adhesive to form a composite, applying the composite to ocular tissue, and activating the light-activated adhesive with light energy.

In an alternative embodiment of the present invention, the method includes the step of combining the light-activated adhesive and a light absorber with deionized water to form a protein solder. In yet another embodiment of the present invention, the method comprises the step of immersing the scaffold material in protein solder. In yet still another embodiment of the present invention, the method further comprises the step of allowing the composite to dry.

In an additional embodiment of the present invention, the method comprises the step of adding a light absorber to the composite. In another embodiment of the present invention, the light absorber includes one of ICG, MB, RFC, BFC, GFC, pH indicators, water, hemoglobin, and photosensitive Rx's.

In a further embodiment of the present invention, the scaffold material includes poly(L-lactic-co-glycolic acid) (PLGA) having an 85:15 lactic:glycolic co-polymer ratio and the light-activated adhesive includes 50% w/v bovine serum albumin (BSA).

In yet another embodiment of the present invention, the applying step includes applying the composite to one of an extraocular muscle—extraocular muscle interface, a sclera—sclera interface, and an extraocular muscle—sclera interface.

In a further embodiment of the present invention, a method for repairing, joining, aligning, or sealing an internal or external wound is provided. The method comprises the steps of combining a biologically compatible scaffold material having at least one irregular surface and a light-activated adhesive to form a composite, applying the composite to a wound, and activating the composite with light energy. The method may also include the step of adding a light absorber to the composite. In certain embodiments, the wound may include aorta, liver, spleen, small intestine, or lung tissue.

BRIEF DESCRIPTION OF THE DRAWINGS

The patent application file contains at least nine (9) drawings executed in color. Copies of this patent or patent application publication with color drawing(s) will be provided by the Office upon request and payment of the necessary fee.

DETAILED DESCRIPTION

Figure 1:
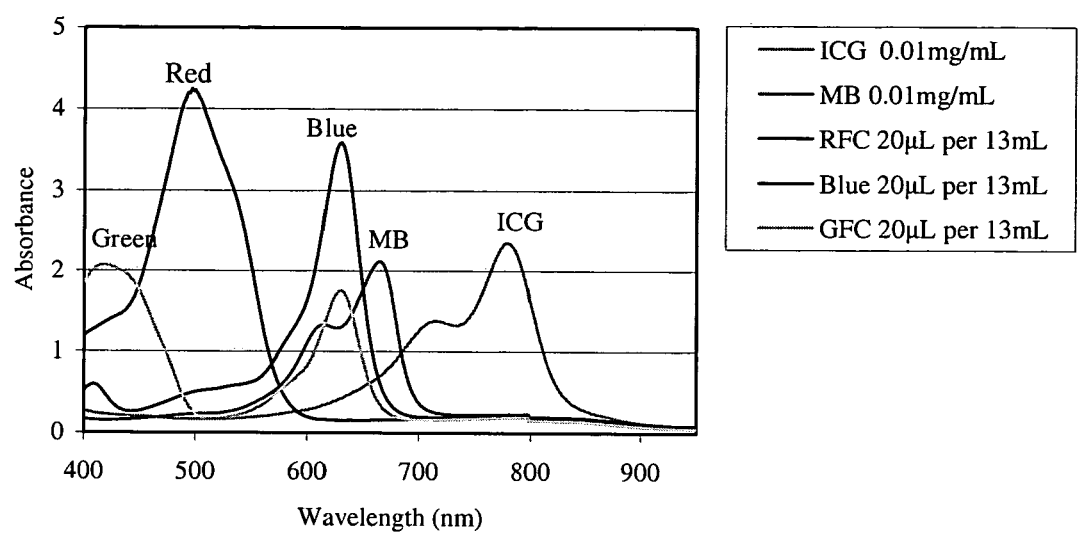
FIG. 1 shows typical absorption spectra of chromophores dissolved in deionized water (refer to Table 1) and scanned using cuvettes with a path length of 10 mm, in the studies described in Example 1.

Several experimental studies have demonstrated the various aspects of the present invention. The attached Appendix, incorporated herein by this reference, includes data tables relating to several of these studies. While specific compounds have been used in the disclosed studies, it is understood that the present invention is not limited to the particular compounds used in any of the disclosed examples.

The scaffold used to form the light-activated composite of the present invention may each be composed of either biologic or synthetic materials. A suitable biological scaffold material comprises SIS (small intestine submucosa), polymerized collagen, polymerized elastin, or other similarly suitable biological materials. Examples of synthetic materials suitable for use as a scaffold include, but are not limited to, various poly(alpha ester)s such as poly(lactic acid) (PLA), poly(glycolic acid) (PGA), poly(L-lactic-co-glycolic acid) (PLGA), poly(.epsilon.-caprolactone) (PCL) and poly(ethylene glycol) (PEG), as well as poly(ortho ester)s and poly (anhydrides).

The scaffold operates to ensure continuous, consistent alignment of apposed tissue edges. The scaffold also helps ensure that the tensile strength of the apposed edges is sufficient for healing to occur without the use of sutures, staples, clips, or other mechanical closures or means of reinforcement. By keeping the tissue edges in direct apposition, the scaffold helps foster primary intention healing and direct re-apposition internally. Thus, the scaffold functions as a bridge or framework for the apposed edges of severed tissue.

In alternative embodiments, the scaffold is engineered for specific applications of the composite by adjusting one or more of its properties. For example, the scaffold includes a smooth surface. Alternatively or in addition, the scaffold includes an irregular surface. Key properties of the scaffold are surface regularity or irregularity, elasticity, strength, porosity, surface area, degradation rate, and flexibility.

For the purposes of this disclosure, "irregular" means that at least a portion of a surface of the scaffold is discontinuous or uneven, whether due to inherent porosity, roughness or other irregularities, or as a result of custom-engineering performed to introduce irregularities or roughness onto the surface (for example, using drilling, punching, or molding manufacturing techniques).

In further embodiments of the present invention, the scaffold is engineered to allow it to function as a depot for various dopants or biologically-active materials, such as antibiotics, anesthetics, anti-inflammatories, bacteriostatic or bacteriocidals, chemotherapeutic agents, vitamins, anti- or pro-neovascular or tissue cell growth factors, hemostatic and thrombogenic agents. This is accomplished by altering the macromolecular structure of the scaffold. For example, its porosity and/or degradation rate can be varied to affect the "rate of delivery" of the dopant.

Examples of suitable light-activated adhesives for use in accordance with the present invention include solid or liquid tissue solders, including protein solders such as serum albumin, fibrinogen, collagen or elastin.

Light energy (e.g., electromagnetic radiation with a wavelength in the range of infrared, visible or ultraviolet light) is delivered to a light-activated adhesive to activate its adhesive properties. Examples of suitable sources of light energy for use in connection with the present invention include lasers having a suitable operating wavelength that would allow the radiation to be absorbed by the solder, and an intense pulsed light source (IPL or IPLS) used in conjunction with suitable optical filters to obtain the desired absorption wavelength range.

Light absorbers are used in laser-tissue soldering to enhance the amount of light energy or radiation that is absorbed by the solder. Chromophores, i.e., chemical groups or residues that impart some decided color to the compound of which it is an ingredient, are one example of light absorbers. The safety of the degradation products of commonly-used chromophores such as indocyanine green (ICG) and methylene blue (MB) following irradiation is uncertain. Also, many chromophores that absorb light will decay with continued exposure to light. The inventors have shown that red, green, and blue food colorings may be used effectively as chromophoric dyes in tissue soldering and have improved degradation characteristics over the commonly-used ICG.

Another alternative light absorber is a pH indicator, such as phenothaline red. Such a pH indicator may be incorporated into the solder material. If the solder material is kept at a pH that does not cause the pH indicator to turn color, the indicator will not absorb light and decay. A small amount of dilute acid or base can be added when the solder material is ready for use, causing the indicator to change color and thus assist in specific light activation.

A pharmaceutical drug that absorbs electromagnetic radiation is used, in yet another embodiment. Such drugs may be used for photochemical or photothermal activation of the adhesive. Any drug or medication that absorbs radiation having a wavelength in the electromagnetic spectrum (including, but not limited to, ultraviolet, visible, or infrared radiation) may be suitable for use as a light absorber and combined with an adhesive. For example, a commercially-available drug such as estradiol, which absorbs light at a wavelength of approximately 400 nm, may be used. Other possible pharmaceutical alternatives include rifampins, licopenes, and phenazopyridine. Such light absorbers offer the additional therapeutic advantage of providing medication to a wound or repair site.

Water, including water contained within the adhesive, is another alternative light absorber. Water absorbs light from a number of infrared sources, including, but not limited to: carbon dioxide ($CO_2$), thulium-holmium-chromium, holmium, thulium and neodymium rare earth doped garnets (THC:YAG, Ho:YAG, Tm:YAG or Nd:YAG), and gallium aluminum arsenide (GaAlAs) diode lasers.

Hemoglobin is yet another alternative light absorber. Hemoglobin absorbs light from a number of sources of visible light, including, but not limited to potassium-titanyl-phosphate (KTP) frequency-doubled Nd:YAG and argon lasers.

Any of the above-mentioned novel combinations of light-activated biological adhesives and alternative light absorbers may be used with or without being combined with a scaffold material. For example, during surgery, there are situations where physicians might prefer to use a light-activated adhesive by itself, such as in plastic surgery involving a face lift or large flap enhancement; or in other surgeries where a deep wound is closed in layers.

Further, the inventors have shown that light-activated adhesives may be used in a wide range of applications, including internal surgeries, external wound closures, and certain ophthalmic surgeries. Studies have been conducted to evaluate the performance of a scaffold-enhanced light-activated solder in ophthalmic applications. Studies have also been conducted to evaluate performance in internal and external applications. Further details are provided in the examples described below.

EXAMPLE 1

Absorption Properties of Alternative Chromophores for use in Laser Tissue Soldering Applications The feasibility of using alternative chromophores in laser tissue soldering (LTS) applications was explored. Two commonly used chromophores, indocyanine green (ICG) and methylene blue (MB), were investigated, as well as three different food colorings: red #40 (RFC), blue #1 (BFC), and green comprising yellow #5 and blue #1 (GFC). Three experimental studies were conducted: (i) The absorption profiles of the five chromophores, when diluted in deionized water and when bound to protein, were recorded; (ii) the effect of accumulated thermal dosages on the absorption profile of the chromophores was evaluated; and (iii) the stability of the absorption profiles of the chromophore-doped solutions when exposed to ambient light for extended time periods was measured.

The peak absorption wavelengths of ICG, MB, RFC, and BFC, were found to be 805 nm, 665 nm, 503 nm, and 630 nm respectively in protein solder. The GFC had two absorption peaks at 417 nm and 630 nm, corresponding to the two dye components comprising this color. The peak absorption wavelength of ICG was dependent on the choice of solvent (deionized water or protein), with an absorption peak of 780 nm in deionized water. In contrast, the peak absorption wavelengths of the other four chromophores were not dependent on the choice of solvent.

ICG and MB showed a significant decrease in absorbance units with increased time and temperature when heated to temperatures up to 100° C. Negligible change in absorption with accumulated thermal dose was observed for any of the three food colorings investigated. Photobleaching was observed in both ICG and MB solutions with exposure to a white light source. An 88% decrease in absorption was seen in ICG deionized water solution after 7 days of exposure with a corresponding 33% decrease in absorption seen in the MB deionized water solution. A negligible drop in absorption was observed from exposure to ambient light for a 12-week period with the three food colorings investigated.

1.1 Chromophore Absorption Profile Study 1.1.1 Preparation of Chromophore Solutions Each of the five chromophores investigated were mixed with deionized water (Fisher Scientific, Hanover Park, Ill.) at five specified concentrations. The five chromophores and the concentrations used for each chromophore are summarized in Table 1.

These concentration ranges were determined experimentally by attempting to scan various concentrations of the chromophores with a UV-Vis-NIR spectrophotometer (Cary 500, Varian Inc., Walnut Creek, Calif.) until a concentration range was determined that was not too concentrated for the 10 mm path length cuvettes (Sigma Chemical Company, St. Louis, Mo.) used in this portion of the study. This spectrophotometer is a double beam, ratio recording spectrophotometer that scans the sample and a blank simultaneously. Significantly higher chromophore concentrations suspended in deionized water created erroneous absorption profiles when used with the 10 mm path length cuvettes. (The preferred operating wavelength range for these cuvettes was 340-800 nm.) Three stock solutions of each concentration were prepared for each of the five chromophores. Five samples of each chromophore concentration were then drawn from each of the three stock solutions and scanned with the spectrophotometer. Once the samples were prepared, they were transferred to the disposable polystyrene cuvettes with stoppers to prevent contamination from foreign matter. The filled cuvettes were stored in their original Styrofoam packaging to prevent light exposure and scratching of the cuvette surface. The samples were scanned with the spectrophotometer directly after preparation to minimize any degradation of the chromophore solution due to light exposure. Data were taken at 1 nm intervals over the spectrum range of 400 to 950 nm.

A smaller sample of much higher concentrations was investigated to determine if the peak absorption wavelength was concentration dependant. The five chromophores and the concentrations used for each chromophore are summarized in Table 2. A single stock solution was prepared for each chromophore and five samples of each concentration were scanned with the spectrophotometer. The cuvettes constructed for this study were prepared using microscope slides (Sigma Chemical Company) with a square cover slip sandwiched in between the slides at both ends of the slides. The slides were placed in a clamp and taped together at the ends after which the clamps were removed. The resultant path length of the cuvettes was 0.15±0.02 mm. The solution was pipetted into the void between the slides immediately before scanning to minimize any degradation of the chromophore solutions.

1.1.2 Preparation of Protein Solder

The absorption profiles of the chromophores when bound to protein were also investigated. Powdered bovine serum albumin was combined with the desired concentration of chromophore and deionized water to produce the protein solder. The chromophore concentrations used in this portion of the study were significantly higher than the concentrations used in the deionized water solutions tested with the 10 mm path length cuvettes. The range of ICG concentrations investigated was taken from studies in the literature using ICG-doped solid protein solders. The concentration range for the other four chromophores was adjusted so that the absorbencies at the peak absorption wavelengths were roughly comparable to the ICG concentration range. The large increase in the chromophore concentration was caused by several factors. The 0.8 mm path length of the solid solder was much shorter than the 10 mm path length of the deionized water study. In addition, an increase in chromophore concentration was required to overcome the natural absorption peaks of the solder itself. The five chromophores and the concentrations used for each chromophore are summarized in Table 3. For each stock solution of chromophore and deionized water used to prepare the protein solder, five samples of each concentration were scanned with the spectrophotometer.

The solid protein solder was mixed using a 60% w/w percentage of albumin to deionized water until it obtained a putty like consistency. The resulting mixture was placed between two clear glass microscope slides and compressed using a parallel plate vice. The resulting protein sheets were 0.80±0.02 mm thick. The specimens were tested within a few hours of preparation to minimize any degradation due to light exposure.

1.2 Thermal Degradation Study

A hot water bath was used to mimic the thermal exposure of the chromophores when irradiated with a laser in photo-thermal LTS applications. This was to distinguish from photochemical LTS applications where the light initiates a chemical reaction causing solder/tissue bonding (i.e., heat is not an issue). Stock solutions were prepared with concentrations of 0.01 mg/mL for ICG and MB, and 20 μL per 13 mL for the food colorings, using the same method described in Section 1.1, and placed in 8 mL clear glass vials with twist on lids. The water bath was heated to the desired temperature of 60, 80 or 100° C., and the glass vials were then suspended in the hot water bath for the allotted time period of 30, 60, 90, 120, 180, 240 or 300 s. Temperature gradients in the water bath were minimized by use of a magnetic stirring rod, and the temperature of the bath was monitored via means of a thermometer suspended in the bath. Upon completion of the allotted time period, the glass vials were removed from the hot water bath and immersed in an ice bath to quickly return the chromophore solutions to near room temperature. The sample solutions were then transferred to disposable polystyrene cuvettes with stoppers to keep out foreign matter. These filled cuvettes were stored in the lightproof Styrofoam container provided with the cuvettes until they were scanned with the spectrophotometer. The samples were scanned immediately after the last sample had been prepared and immersed in the hot water bath. Five samples of each chromophore, temperature and time combination were analyzed.

1.3 Light Exposure Study

Chromophore solutions were exposed to an illuminated 60 W incandescent light bulb for varying periods of time to examine the effect of light exposure on their absorption profiles. Two stock solutions of each chromophore were prepared with concentrations of 0.01 mg/mL for ICG and MB, and 20 μL per 13 mL for the food colorings, using the same method described in Section 1.1. One stock solution of each chromophore was placed in a 130 mL clear glass jar, with the lid tightened firmly to prevent evaporation. The jars were placed in a single file line on a laboratory bench, about a foot away from the bulb, so that they were approximately perpendicular to the light source. The other stock solution for each chromophore was used as a control group. The control solutions were stored in 130 mL amber glass bottles within a closed cardboard box to minimize light exposure. Exposure periods were 0, 7, 14, 28, 56, and 84 days. A separate study containing only ICG and MB were tested daily from 0 to 7 days. Five samples of each chromophore were scanned with the spectrophotometer for each time period.

1.4 Results: Chromophore Absorption Profile Study

The absorption profiles of the five chromophores, both diluted in deionized water and bound to protein, were recorded with a Cary 500 UV-Vis-NIR spectrophotometer. Data were taken at 1 nm intervals over the spectrum range of 400 to 950 nm.

1.4.1 Chromophore Dissolved in Deionized Water

Figure 2:
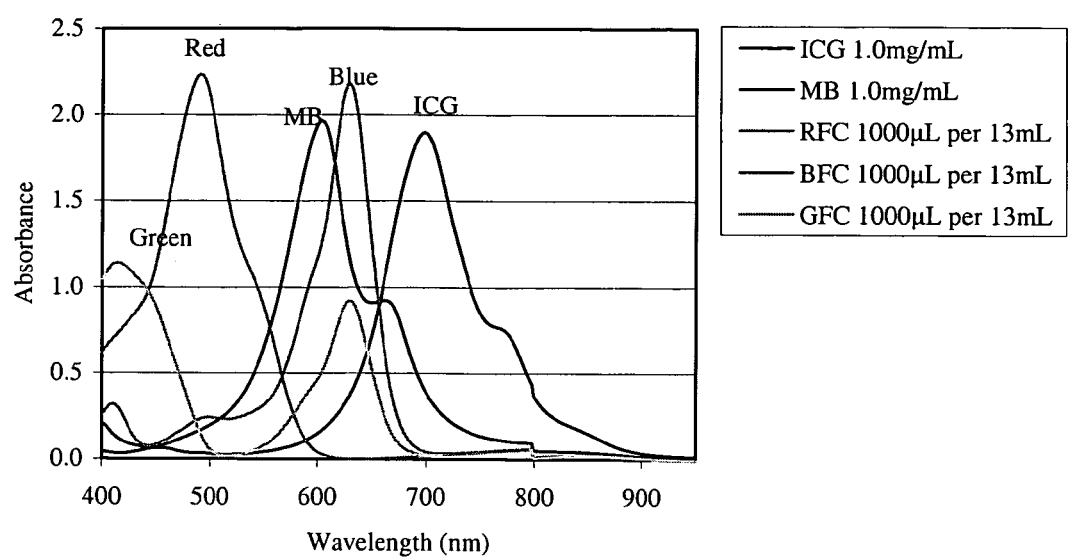
FIG. 2 shows typical absorption spectra of chromophores dissolved in deionized water (refer to Table 2) and scanned using cuvettes with a path length of 0.15 mm, in the studies described in Example 1.

Typical absorption spectra for the highest concentration of each of the chromophores dissolved in deionized water and scanned with the long path length (10 mm) cuvettes (refer to Table 1) are shown in FIG. 1. The absorption spectra for the highest concentration used in the short path length (0.15 mm) study (refer to Table 2) are shown in FIG. 2. The food colorings did not exhibit a characteristic shift in peak absorption wavelength with increased concentration in deionized water solution. The peak absorption of MB in deionized water solution decreased from 666 to 603 nm over the concentration range of 0.001 to 1.0 mg/mL. Likewise, the peak absorption of ICG in deionized water solution decreased from 781 to 698 nm over the concentration range of 0.001 to 1.0 mg/mL. This shift in peak absorption wavelength found in ICG and MB is caused by the progressive formation of aggregates as the concentration of the chromophore is increased.

1.4.2 Chromophore Bound to Serum Albumin

Figure 3:
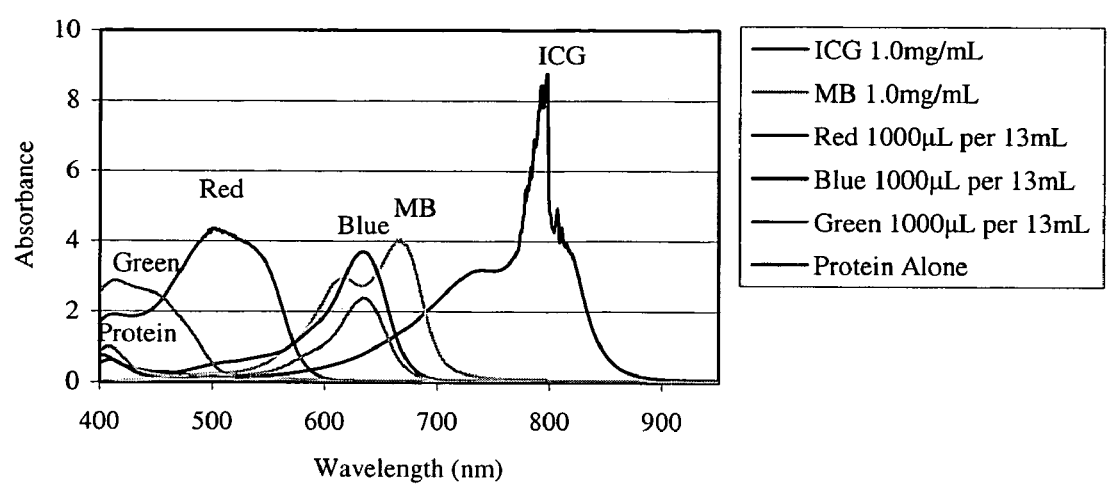
FIG. 3 shows typical absorption spectra for chromophores mixed with 60% w/w BSA protein solder (refer to Table 3) and scanned using a path length of 0.80 mm, in the studies described in Example 1.

Typical absorption spectra for the highest concentration of each of the chromophores mixed with 60% w/w BSA protein solder (path length=0.80 mm) (refer to Table 3) are shown in FIG. 3. At concentrations ranging from 0.001 to 1.0 mg/mL, the peak wavelength of the ICG spectrum displayed its characteristic shift from 780 nm in deionized water to 805 nm when bound to protein as discussed in the literature. A shift in peak absorption wavelength was also observed with MB. At a concentration of 1.0 mg/mL, the peak absorption of MB in deionized water was 603 nm, while when bound to protein, the peak absorption of MB was 665 nm (refer to FIGS. 2 and 3), similar to the lower concentration absorption spectra seen in FIG. 1. No shift in the peak absorption wavelength of MB when bound to protein was seen for concentrations of 0.001 to 0.01 mg/mL. As seen in FIG. 3, the shoulder of the MB spectra at approximately 665 nm remains dominant in this higher concentration range when MB is bound to protein. The other three chromophores did not exhibit a shift in peak absorption wavelength when bound to protein.

1.5 Results: Thermal Degradation Study

Figure 4:
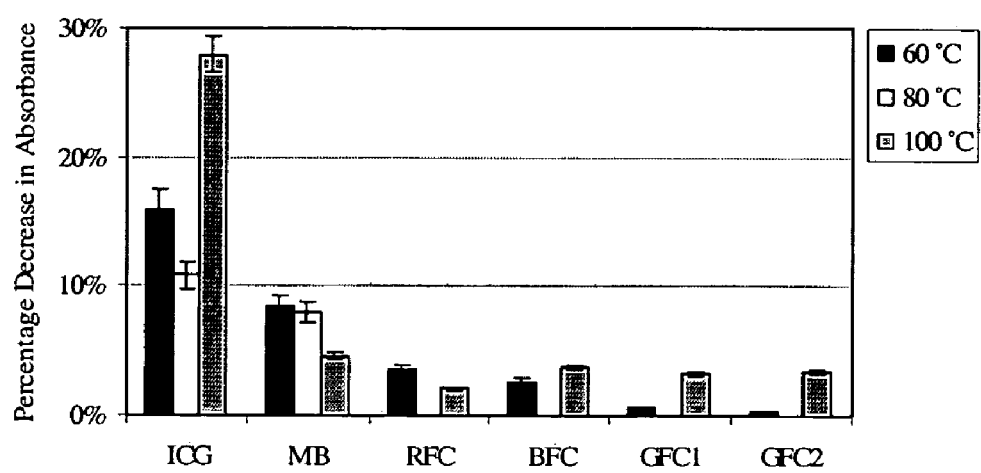
FIG. 4 shows the percentage decrease in absorbance at peak wavelength recorded from chromophore-doped deionized water solutions that were heated at set temperatures for a period of 300 s in the studies described in Example 1.

The results of the thermal denaturation study for each of the five chromophores investigated are summarized in Tables 4 and 5A-5B. Table 4 summarizes the changes in absorbance at peak wavelength recorded when deionized water solutions containing ICG and MB were heated to temperatures of 60, 80, or 100° C. for various periods of time. Tables 5A-5B present the changes in absorbance at peak wavelength recorded when deionized water solutions containing food coloring were heated to temperatures of 60° C. or 100° C., for various periods of time. A graphical representation of these results is shown in FIG. 4. The ICG deionized water solutions experienced, on average, a 28% decrease in absorbance units after 300 seconds at 100° C., the maximum thermal exposure investigated in this study. The remaining four chromophores experienced, on average, less than a 3.3% decrease in absorbance units after maximum thermal exposure. Although an analysis of variance test indicates a significant change in absorption with accumulated thermal dose for all temperature ranges of ICG, the 100° C. group showed a much larger decrease in absorbance units with increased time and temperature than the 60° C. and 80° C. groups. A negligible change in absorption with accumulated thermal dose was observed for MB and all of the food colorings investigated.

1.6 Results: Light Exposure Study

Figure 5A:
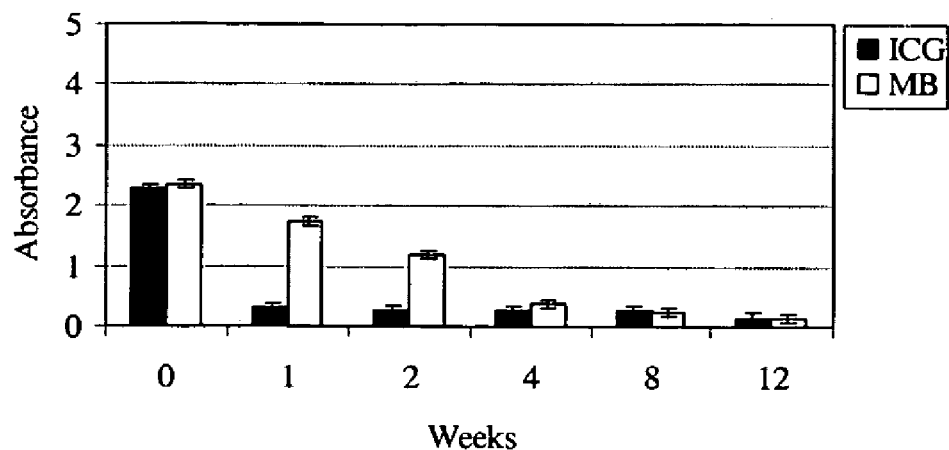
FIGS. 5A and 5B show absorbance at peak wavelength recorded from chromophore-doped deionized water solutions after exposure to light for specified time periods, during the studies described in Example 1.
Figure 5B:
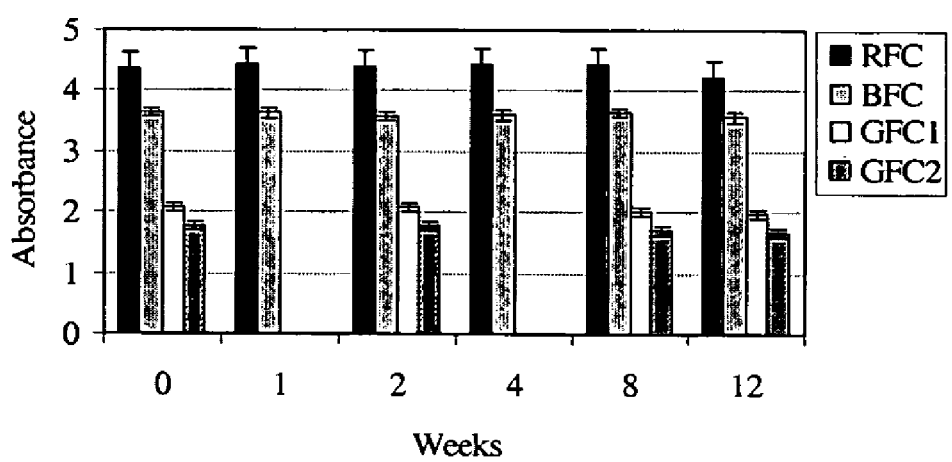

Several studies have explored the degradation of ICG solutions with exposure to light. An initial study was conducted on the five chromophores being investigated in this study to evaluate possible degradation due to exposure to light. Experimental and control solutions (refer to Section 1.3) (two different stock solutions) were tested on days 0, 7, 14, 28, 56, and 84. The results of this study are summarized in Tables 6A and 6B. A graphical representation of this data is shown in FIGS. 5A and 5B.

Figure 6A:
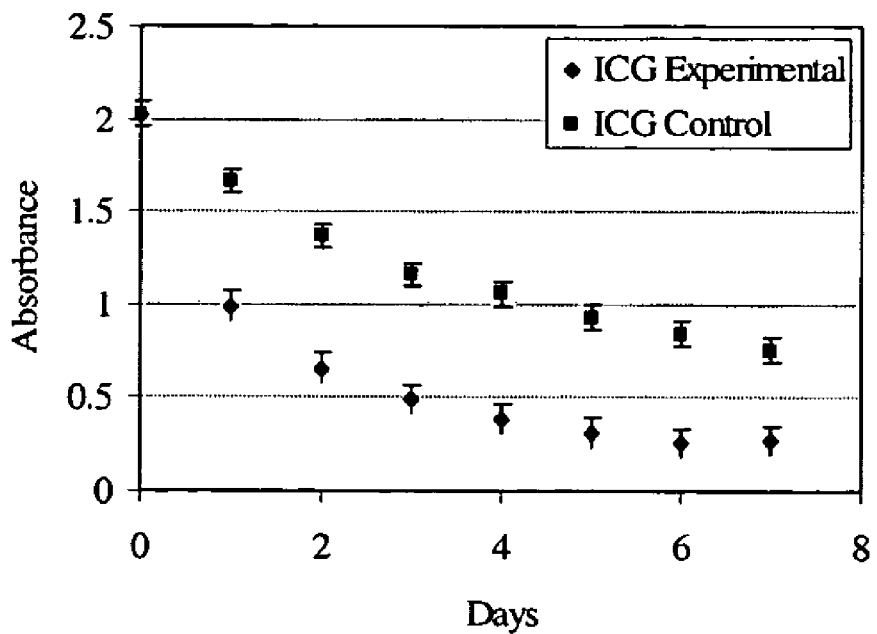
FIGS. 6A and 6B show absorbance at peak wavelength recorded when deionized water solutions containing 0.01 mg/mL ICG and MB were exposed to white light for a period up to 7 days, in the studies described in Example 1.
Figure 6B:
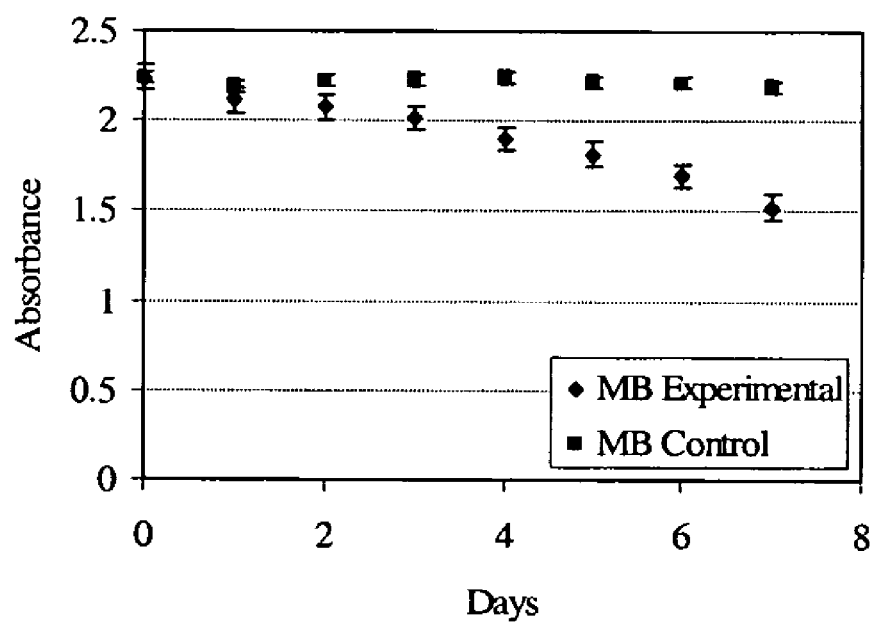

The relatively quick degradation of the ICG and MB solutions compared to the food colorings prompted a shorter term study to evaluate the degradation of these two chromophores on a daily basis over a period of seven days of exposure. The results of this study are shown in FIGS. 6A-6B. The ICG solution experienced the largest drop in absorbance during the first day in both the experimental and the control groups, with a total loss of absorbance of 87.5% over the seven-day period. MB experienced a 33% loss of its absorbance during the same period.

1.7 Conclusions

Each of the food colorings investigated have absorption peaks near the operating wavelength of existing lasers. RFC has an absorption peak ($\lambda$=500 nm) that would allow for its use with coumarin dye, Cu Vapor, Ar Ion or Kr Ion lasers. BFC has an absorption peak ($\lambda$=630 nm) that allows for its use with a rhodamine dye, HeNe, Au Vapor or Kr Ion laser. The absorption peaks of GFC ($\lambda$=417 nm and 630 nm) allow for its use with many different laser systems including a stilbene dye laser, or Kr Ion laser in addition to the lasers mentioned for use with the blue food coloring. Each food coloring investigated demonstrated consistent peak absorption wavelengths when mixed either in deionized water solution or with albumin protein solder. Another attractive feature of these alternative chromophores is their lack of degradation due to heat and light exposure. Use of these chromophores would cause the protein in the solder to be the limiting factor on the shelf life of chromophore-doped protein solders.

ICG showed a significant decrease in absorbance units with increased time and temperature when heated up to temperatures of 100° C. The absorbance of ICG specimens heated at 100° C. in the present study dropped from 1.85 to 1.34 after a period of 300 s. The time frame investigated in the present study is more consistent with that used in LTS applications. Although statistically all of the chromophores were in some way affected by temperature, the difference in absorption of ICG and MB was much more evident in this time frame than it was for the three food colorings investigated. Use of the alternative chromophores seems advantageous due to the improved stability of their absorption profiles with accumulated thermal dosages.

The absorbance of ICG in deionized water solution fell from 2.02 to 1.06 after only one day of exposure to white light, and to 0.26 after seven days of exposure. In comparison, the absorbance of the control solution fell to 1.69 and 0.75 after one and seven days, respectively. Likewise, MB also experiences some degradation from exposure to light. The absorbance of the MB solution fell from 2.24 to 2.15 after one day of exposure to white light, and to 1.48 after seven days of exposure. In comparison, the absorbance of the control solution fell to 2.13 and 2.17 after one and seven days, respectively. The absorption profiles of ICG and MB experimental groups as well as the ICG control group had no discernable peaks after 84 days. The MB control group maintained its absorbance after 84 days (refer to Tables 6A and 6B). The three food colorings did not display a large loss of absorption after 84 days. This property makes the food colorings particularly attractive for LTS applications as, in contrast to ICG and MB, the chromophores would not be the limiting factor on determining the shelf life of the protein solders.

In summary, the alternative chromophores have absorption profiles that are compatible with existing laser sources, but show negligible degradation with either light or thermal exposure.

EXAMPLE 2

Effect of Varying Chromophores Used in Light-Activated Protein Solders on Tensile Strength and Thermal Damage Profile of Repairs The use of indocyanine green-doped albumin protein solders has been shown to vastly improve the anastomotic strength that can be achieved by laser tissue repair techniques, while at the same time minimizing collateral thermal tissue damage. However, the safety of the degradation products of this chromophore following laser irradiation is uncertain. Experimental investigations were thus conducted to test the tensile strength of ex vivo tissue repairs formed after laser tissue soldering using solders doped with alternative chromophores including two different food colorings: blue #1 (BFC) and green comprising yellow #5 and blue #1 (GFC) in a bovine model. Two commonly used chromophores, indocyanine green (ICG) and methylene blue (MB), were investigated as a reference. In addition, the temperature rise, depth of thermal coagulation in the protein solder, and the extent of thermal damage in the surrounding tissue were measured.

Temperature rise at the solder surface and at the interface between the solder and tissue were monitored by a non-contact infrared temperature monitoring system and a type-K thermocouple, respectively, and the extent of thermal damage in the underlying tissue was determined using light microscopy. As expected, temperature rise at the solder/tissue interface, and consequently the degree of collateral thermal tissue damage, was directly related to the penetration depth of the laser light in the protein solder. Variation of the chromophore concentration such that the laser light penetrated to a depth approximately equal to half the thickness of the solder resulted in uniform results between each group of chromophores investigated. Optimal tensile strength of repairs was achieved by selecting a chromophore concentration that resulted in a temperature of 66±3° C. at the solder/tissue interface.

The two alternative chromophores tested in this study show considerable promise for application in laser tissue soldering techniques, with equivalent tensile strength to solders doped with ICG or MB, and the potential advantage of eliminating the risks associated with harmful byproducts.

2.1 Preparation of Chromophore-Doped Scaffold-Enhanced Solder

Protein solder was prepared by combining 50% bovine serum albumin (BSA) (Sigma Chemical Company, St. Louis, Mo.) with the desired concentration of chromophore in deionized water. The four chromophores, ICG, MB, BFC and GFC, and the concentrations used for each chromophore, are summarized in Table 7. The concentration range for the other four chromophores was adjusted such that the absorbancies at the peak absorption wavelengths were roughly comparable to those observed within the range of ICG concentrations. The solder was placed in light-proof plastic vials and stored in a refrigerator at 4° C. until needed. Solder remaining after three days was discarded.

Porous synthetic polymer scaffolds were fabricated using PLGA with a solvent casting and particulate leaching technique. Two hundred milligrams PLGA (Sigma Chemical Company) was dissolved in dichloromethane and subsequently mixed with 467 milligrams sodium chloride (70% weight fraction, particle size 106-150 μm). The polymer was then poured into a 60 mm diameter Petri dish and left beneath a fume hood for 24 hours to allow the dichloromethane to evaporate. Upon drying, the scaffolds were immersed in deionized water three to four times over a 24-hour period to leach out the salt particles, leaving behind the porous polymer scaffolds. After removing the scaffolds from the Petri dishes, they were left to air dry and then stored until needed. Prior to use for tissue repairs, the polymer scaffolds were cut into 10 mm by 5 mm rectangular pieces and subsequently soaked in the BSA protein solder for two hours. The average thicknesses of the chromophore-doped scaffold-enhanced solders, determined by scanning electron microscopy (Hitachi S-3000N Scanning Electron Microscope, Hitachi Scientific Systems Ltd., Hitachinaka, Japan) and measurement with precision calipers (L.S. Starrett Co., Anthol, Mass.), were in the range of 145 to 155 μm.

2.2 Optical Penetration Depth of Laser Light in Chromophore-Doped Scaffold-Enhanced Solders The peak absorption wavelengths of ICG, MB, BFC and GFC when bound to protein are listed in Table 8, along with the corresponding laser systems used in this study.

Specimens of the chromophore-doped scaffold-enhanced solders were pressed between two glass slides to form a slab having dimensions of 2×2 cm with an approximate thickness of 150 μm. Total transmission and diffuse reflection were measured on five samples of each of the chromophore-doped scaffold-enhanced solder specimens using a UV-Vis-NIR spectrophotometer (Cary 500, Varian Instruments, Walnut Creek, Calif.), equipped with an integrating sphere. The diffusion approximation with a delta-Eddington phase function that assigns forward scattered light into a delta function, and the predetermined refractive indices for albumin protein solder reported in a previous study, were input into Prahl's iterative program for inverse adding-doubling to determine the absorption and reduced scattering coefficients of each of the chromophore-doped scaffold-enhanced solders. The program computed the diffuse reflection and total transmission for an assumed pair of values for absorption and reduced scattering coefficients. Prahl's program considered multiple reflections that occurred at air/slide/solder/slide/air interfaces. New values of the absorption coefficient, $\mu_a$ (in inverted meters), and the reduced scattering coefficient, $\mu_s'=\mu_s(1-g)$ (in inverted meters), were automatically computed until reflection and transmission matched measured values. The scattering coefficient, $\mu_s$, was also calculated with the anisotropy factor, g (no units), assumed to be ~0.80, as determined for BSA solder in a previous study. From these measurements, the optical penetration depth (OPD) ($\delta=1/(\mu_a+\mu_s')$) in the chromophore-doped scaffold-enhanced solders of each of the corresponding laser wavelengths was calculated for a thickness of approximately 150 μm.

2.3 Laser-Solder Repair Technique

Bovine thoracic aortas were obtained from a local slaughterhouse. The aortas were washed in phosphate buffered saline and cut into rectangular pieces with dimensions of 2.5×1.5 cm. The excess adventitia was trimmed to obtain a specimen thickness of approximately 1 mm. Laser-soldering was conducted on the intima of the aorta. A full thickness incision was cut through the specimen width using a scalpel and opposing ends were placed together. A strip of chromophore-doped scaffold-enhanced solder was then placed over the incision and thermally bonded to the tissue by means of light activation with the corresponding laser. Each laser was operated in continuous mode with a spot-size at the solder surface of approximately 1 mm for the 808 nm and 670 nm diode lasers, and 0.5 mm for the 632.8 nm diode laser. An irradiance of approximately 15.9 W/cm², measured using a Fieldmaster GS power meter with a LM100 thermopile detector (Coherent Scientific, Santa Clara, Calif.), was delivered to the surface of the solder. The laser beam was scanned in a continuous spiral pattern across the solder two times (starting from the center). The approximate exposure time for each repair was 80±5 s. Ten repairs were performed for each chromophore concentration investigated (refer to Table 7).

2.4 Temperature Analysis

2.4.1 Solder Surface and Solder/Tissue Interface Temperature Measurements

The total temperature difference across the adhesive material was determined using a non-contact pyroelectric detector and a 0.5 mm type-K thermocouple to measure the temperature reached at the protein solder surface and at the solder/tissue interface, respectively. The pyrodetector was designed to have highest sensitivity to wavelengths in the 8 to 12 μm range. Blackbody radiation emitted from the repair site was guided to the pyrodetector via a silver halide ($AgCl_xAgBr_{1-x}$) core-clad fiber with a core diameter of 700 μm. A custom hand-piece held the laser delivery and radiometer fibers together, allowing the fibers to be fixed facing the same spot. The system was calibrated from 30 to 150° C. using black bodies of known temperature and using the assumption that the emissivity of the solder was approximately equal to 1.0. The minimum resolvable temperature difference (MRTD) and response time of the pyrodetector over this range were 1° C. and 10 ms, respectively. The MRTD and response time of the thermocouple were 0.5° C. and 50 ms, respectively.

2.4.2 Light Microscopy

Light microscopy was used to determine the depth of thermal damage in the underlying tissue substrate as a result of the laser treatment. Masson's Trichrome and Hematoxylin and Eosin (H&E) were used as the staining agents. The depth of damage in the tissue substrates was estimated using two criteria: (i) a color change in the tissue collagen from green to crimson (Masson's Trichrome staining) signifying denaturation; and (ii) structural variations such as swelling of collagen fibers in the tissue (H&E staining). The more subtle indications of damage including cellular shrinkage and conformational changes were neglected. Uncertainty in the measurements is attributed to variations in the level of staining achieved with the different batches of stains and small variations in the physiological structure of individual specimens.

2.5 Tensile Strength Analysis

Tensile strength measurements were performed to test the integrity of the resultant repairs immediately following the laser procedure using a calibrated MTS Material Strength Testing machine (858 Table Top System, MTS, Eden Prairie, Minn.). This system was interfaced with a personal computer to collect the data. Each tissue specimen was clamped to the strength testing machine using a 100N load cell with pneumatic grips. The specimens were pulled apart at a rate of 1 gravitational force/sec until the repair failed. Complete separation of the two pieces of tissue defined failure. The maximum load in Newton's was recorded at the breaking point. In order to avoid variations in repair strength associated with drying, the tissue specimens were kept moist during the procedure.

2.6 Results

Figure 7A:
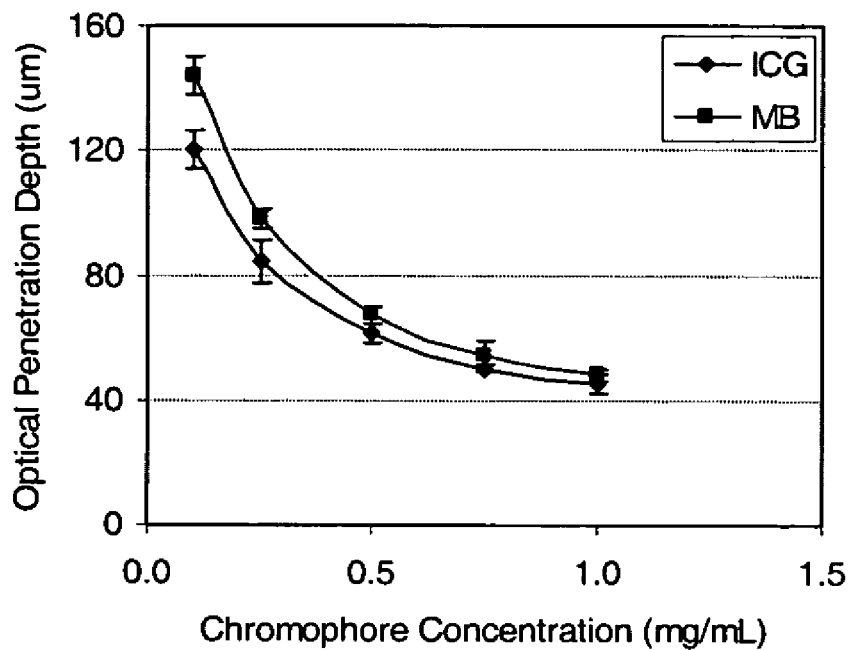
FIG. 7A is a graph of the chromophore concentration and optical penetration depth (OPD) using 808 nm light in the ICG-doped and 670 nm light in the MB-doped scaffold-enhanced solder of Example 2.
Figure 7B:
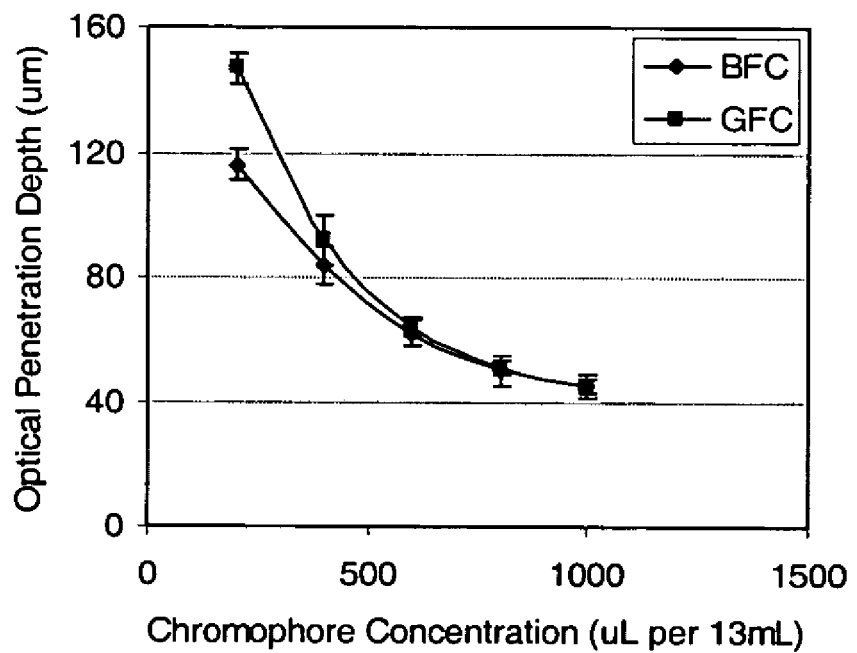
FIG. 7B is a graph of the chromophore concentration and optical penetration depth (OPD) using 632.8 nm light in the BFC-doped and GFC (#1)-doped scaffold-enhanced solder of Example 2.
Figure 8A:
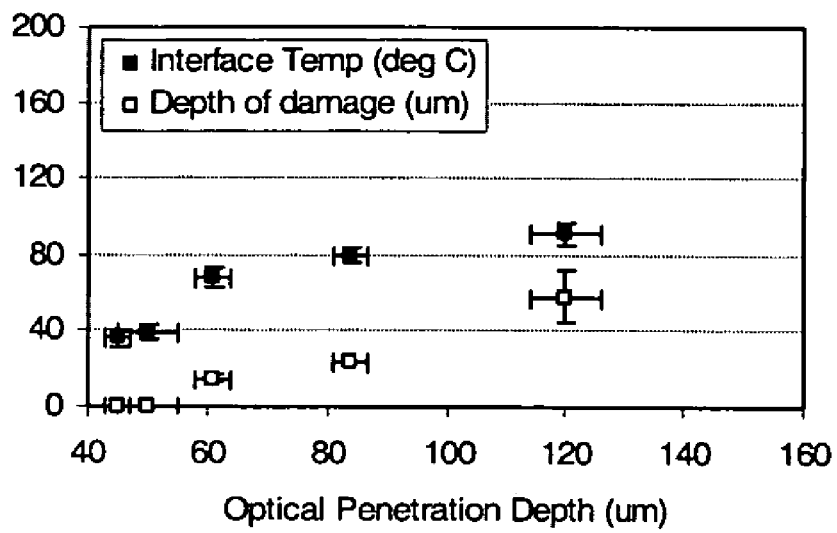
FIGS. 8A-8D show solder/tissue interface temperature and depth of thermal damage in the tissue substrate expressed as a function of OPD (refer to FIG. 7) resulting from the studies described in Example 2, as follows: (a) ICG-doped scaffold-enhanced solder used in conjunction with an 808 nm diode laser; (b) MB-doped scaffold-enhanced solder used in conjunction with a 665 nm diode laser; (c) BFC-doped scaffold-enhanced solder used in conjunction with a 632.8 nm diode laser; and (d) GFC (#1)-doped scaffold-enhanced solder used in conjunction with a 632.8 nm diode laser. Lower chromophore concentrations correspond to higher OPD's. Each point represents the mean and standard deviation for ten repairs.
Figure 8B:
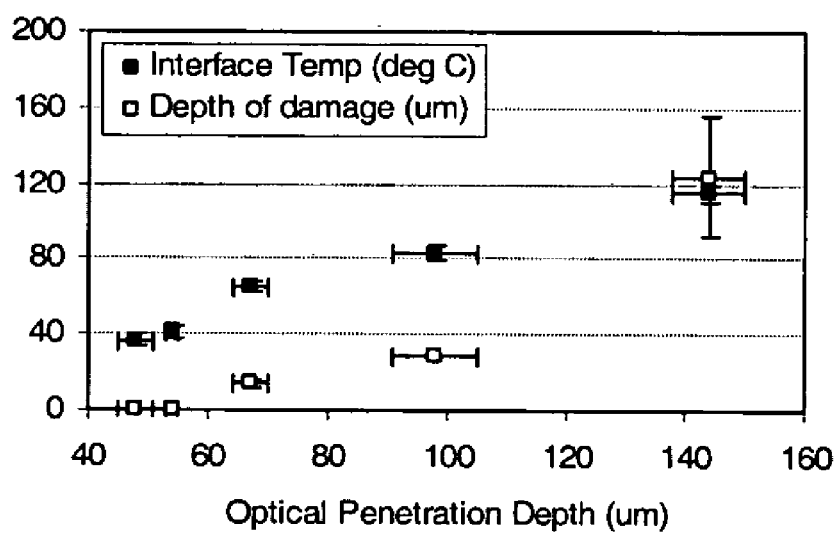
Figure 8C:
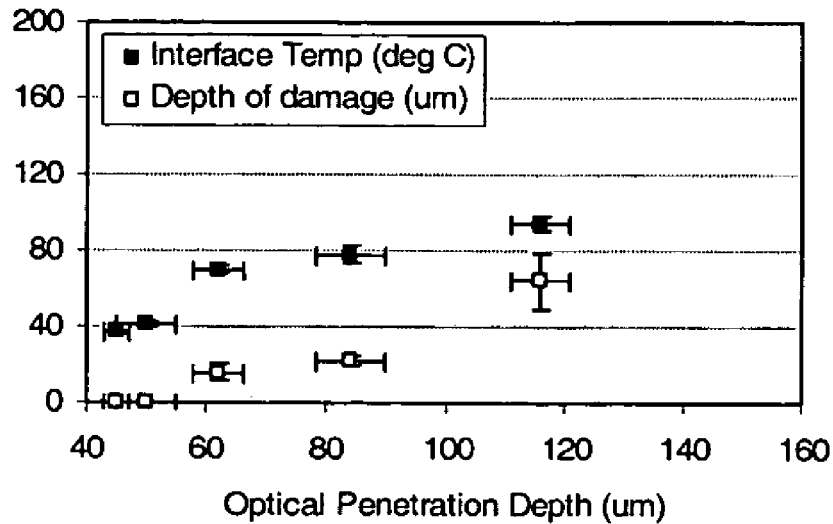
Figure 8D:
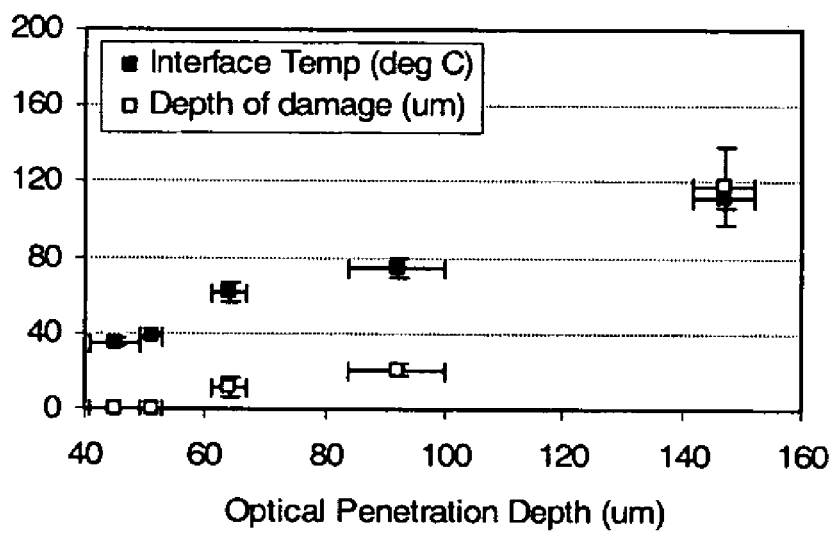
Figure 9A:
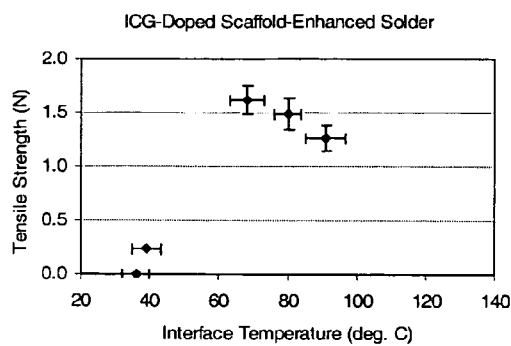
FIGS. 9A-9D show the tensile strength of repairs performed using chromophore-doped scaffold-enhanced solders as a function of interface temperature in the studies described in Example 2, as follows: (a) ICG-doped scaffold-enhanced solder used in conjunction with an 808 nm diode laser; (b) MB-doped scaffold-enhanced solder used in conjunction with a 665 nm diode laser; (c) BFC-doped scaffold-enhanced solder used in conjunction with a 632.8 nm diode laser; and (d) GFC (#1)-doped scaffold-enhanced solder used in conjunction with a 632.8 nm diode laser. Lower chromophore concentrations correspond to higher OPD's, and subsequently, higher interface temperatures. Each point represents the mean and standard deviation for ten repairs.
Figure 9B:
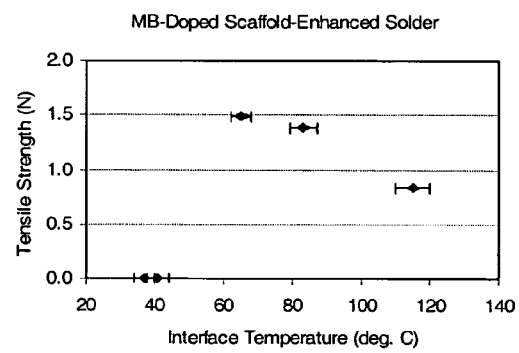
Figure 9C:
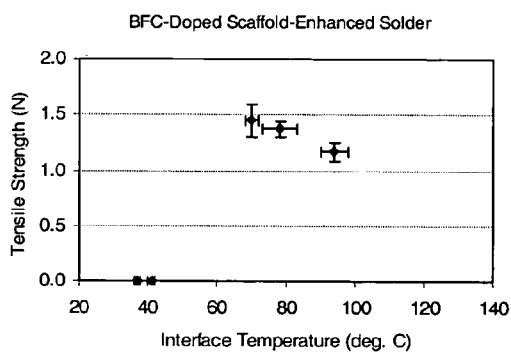
Figure 9D:
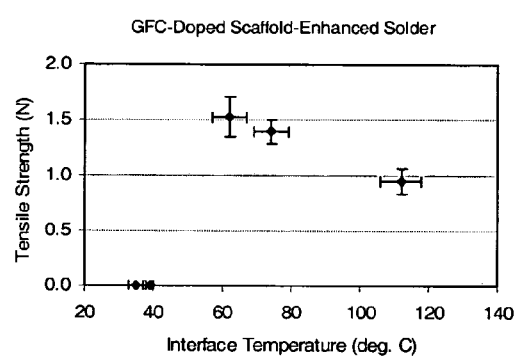

The OPD's of each of the four chromophores are presented in FIGS. 7A and 7B as a function of chromophore concentration. As specified in Section 2.1, the thicknesses of the solder-impregnated polymer scaffolds were in the range of 145 to 155 μm.

FIGS. 8A-8D summarize the results of studies conducted to determine the temperature at the solder/tissue interface and the degree of collateral thermal damage in the underlying tissue as a result of the laser procedure. As can be seen in these graphs, temperature rise at the solder/tissue interface, and consequently the degree of collateral thermal tissue damage, was directly related to the penetration depth of laser light in the chromophore-doped scaffold-enhanced solder.

The tensile strength of repairs performed using the chromophore-doped scaffold-enhanced solders are summarized in FIGS. 9A-9D as a function of the temperature reached at the solder/tissue interface during the laser procedure. The tensile strength of repairs was optimized by selecting a chromophore concentration that resulted in a temperature of 66±3° C. at the solder/tissue interface. The optimal concentrations were 0.5 mg/mL for ICG and MB, and 600 μL per 13 mL for BFC (#1) and GFC (#1). At these concentrations, the OPD's were recorded to be 61±3 μm, 67±3 μm, 62±4 μm and 64±3 μm, respectively.

2.7 Conclusions

Focus on blue and green food colorings as alternative chromophores is based on the fact that they have absorption peaks near the operating wavelength of existing laser systems. The blue food coloring absorption peak (λ=630 nm) allows for its use with rhodamine dye, HeNe, Au Vapor, and Kr Ion lasers. The absorption peaks of the green food coloring (λ=417 nm and 630 nm) allow for its use with many different laser systems including a stilbene dye laser, or Kr Ion laser in addition to the lasers mentioned for use with the blue food coloring. Each food coloring investigated demonstrated consistent peak absorption wavelengths when mixed either in deionized water solution or with albumin protein solder.

Another attractive feature of these alternative chromophores is the lack of degradation due to heat and light exposure. ICG and MB, on the other hand, showed a significant decrease in absorbance units with increased time and temperature when heated to temperatures up to 100° C. Photo bleaching was also observed in both ICG and MB solutions with exposure to a white light source. An 88% decrease in absorption was seen in ICG deionized water solution after 7 days of exposure with a corresponding 33% decrease in absorption seen in the MB deionized water solution. Use of these chromophores would cause the protein in the solder to be the limiting factor on the shelf life of the chromophore-doped scaffold-enhanced solders. Other colors could also be used for the same purpose. For example, while red food coloring (RFC) was not investigated in this study due to the lack of availability of a suitable laser source, it too is a feasible chromophore as its absorption peak (λ=500 nm) would allow it to be used with coumarin dye, Cu Vapor, Ar Ion, and Kr Ion lasers.

Temperature rise at the solder/tissue interface, and consequently the degree of collateral thermal tissue damage, was directly related to the OPD of the laser light in the protein solder. Variation of the chromophore concentration such that the OPD was 64±3 μm, corresponding to a little less than half the thickness of the chromophore-doped scaffold-enhanced solder, resulted in uniform results between each group of chromophores, and produced optimal results in terms of minimal thermal damage and maximal tensile strength of repairs. These results are supported by Beer's law, which shows that 85% of laser energy is absorbed within twice the OPD of a material.

At the higher chromophore concentrations investigated (0.75-1.0 mg/mL ICG or MB and 800-1000 μL per 13 mL BFC or GFC), the laser energy was deposited in the superficial volume of the scaffold-enhanced solder, resulting in a large accumulation of heat at the surface of the solder before it was conducted to the solder/tissue interface. Heat transfer is proportional to the temperature gradient across the solder, as described by Fourier's law, and thus, insufficient heat transfer to the vital solder/tissue interface occurred to provide adequate solder-tissue bonding. In fact, repairs formed using these chromophore concentrations were barely strong enough to handle the manipulation required to load them on the material strength testing machine. Low chromophore concentrations (0.1-0.25 mg/mL ICG or MB and 200-400 μL per 13 mL BFC or GFC) with corresponding long OPD's resulted in extensive thermal damage to the underlying tissue and consequently, weaker repairs.

Optimal tensile strength of repairs was achieved by selecting a chromophore concentration that resulted in a temperature of approximately 66±3° C. at the solder/tissue interface. These results are in agreement with previous research conducted to investigate the thermal damage processes that occur in BSA, which show that serum albumin denatures between approximately 60 and 70° C.

The two alternative chromophores investigated in this study, BFC and GFC, produced equivalent results to ICG in terms of collateral thermal tissue damage and optimal tensile strength of repairs when used in scaffold-enhanced solders for laser-assisted vascular repairs. In addition, the properties of these alternative chromophores appear to have attractive qualities compared to the commonly used ICG chromophore. For example, the alternative chromophores do not degrade in a deionized water solution or when bound to protein with exposure to ambient light, nor do they degrade with time. The improved stability of these alternative chromophores is encouraging for the improvement of laser-assisted tissue repair techniques.

EXAMPLE 3

A Light-Activated Surgical Adhesive Technique for Sutureless Ophthalmic Surgery

Suture use in ophthalmic surgery is technically-demanding, time-consuming and may be associated with serious complications, such as inadvertent ocular penetration which can result in retinal detachment and endophthalmitis. Bioadhesive surgery could eliminate many complications and limitations associated with the use of sutures. We investigated a scaffold-enhanced light-activated bioadhesive technique as a substitute for sutures in ophthalmic surgery.

The bioadhesive was composed of a poly(L-lactic-co-glycolic acid) (PLGA) porous scaffold impregnated with a protein solder mix composed of serum albumin and indocyanine green (ICG) dye, which was activated with a diode laser. Extraocular rectus muscle-to-extraocular rectus muscle, sclera-to-sclera and extraocular rectus muscle-to-sclera adhesions were created in freshly-harvested tissue followed by acute tensile strength testing of these surgical adhesions.

Optimum tensile strength for extraocular rectus muscle-to-extraocular rectus muscle repair was achieved with 50% w/v BSA and 0.5 mg/ml of ICG saturated into a PLGA porous scaffold and activated with an 805 nm diode laser. Tensile strength was 81% of native muscle tensile strength (4.2±0.69 N vs. 4.8±0.72 N). Sclera-to-sclera adhesions achieved a breaking load of 2.9±0.37 N, while extraocular rectus muscle-to-sclera was 3.0±0.36 N.

Sutureless surgery utilizing this bioadhesive technique for various ophthalmic procedures may result in reduced surgical complications and cost.

3.1 Experimental Groups

Three experimental groups were investigated: bonding of (I) extraocular rectus muscle-to-extraocular rectus muscle (four subgroups with n=10 each), (II) sclera-to-sclera (n=20), and (III) extraocular rectus muscle-to-sclera (n=20). In the first experimental group, rabbit superior rectus muscles were harvested approximately 45 minutes after sacrificing the animals. Tissue specimens were stored in phosphate buffered saline for a maximum of four hours at 4° C. before they were prepared for experiments. In the second group, eye bank human sclera was obtained and stored in phosphate buffered saline for a maximum of two days at 4° C. prior to use. In the third group, porcine eyes were obtained from a slaughterhouse approximately 4 hours after sacrificing the animals and stored in phosphate buffered saline for a maximum of two days at 4° C. before being utilized.

3.2 Preparation of the Surgical Adhesive

Porous synthetic polymer scaffolds were prepared from PLGA, with a lactic:glycolic acid ratio of 85:15, using a solvent casting and particulate leaching technique. The scaffolds were cast by dissolving 200 mg PLGA in 2 ml dichloromethane. Sodium chloride (salt particle size: ≦106 μm or 106-150 μm) with a 70% weight fraction was added to the polymer mix. The polymer solution was then cast in a 60 mm Petri dish and left in a fume hood for 24 hours to allow the dichloromethane to evaporate. The salt was leached out of the polymer scaffolds, by immersion in filtered deionized water for 24 hours, to create the porous scaffolds. During this period the water was changed 3 to 4 times at approximately 2 hour intervals. The scaffolds were then air-dried and stored at room temperature until required.

Protein solder was prepared from either 25%(w/v) or 50% (w/v) BSA (Cohn Fraction V) and ICG dye at a concentration of 0.5 mg/ml, mixed in deionized water. The compounds were used without further purification. The solder was stored in lightproof plastic vials at 4° C. until required. Solder not used within one week was discarded.

The PLGA scaffolds were cut into rectangular pieces with the desired dimensions. The scaffolds were left to soak for a minimum of two hours in the protein solder mix before use. The thickness of the solder-impregnated polymer scaffolds, determined by scanning electron microscopy and measurement with precision calipers, was in the range of 200 to 205 μm.

3.3 Tissue Repair Procedure

Group I: Extraocular Rectus Muscle-to-Extraocular Rectus Muscle Adhesion

The length and thickness of each muscle specimen was 8.0±2.0 mm and 1.5±0.1 mm, respectively. A complete transection (n=40) was accomplished with a #15 Bard-Parker blade and opposing ends were placed together on a piece of parafilm. Four sets of adhesive fabrication parameters were studied. Each parameter set differed in protein concentration and scaffold porosity (Table 9). These groups were tested in a two-factor two-level experimental design. Subset A utilized a 25% w/v albumin solder with a scaffold pore size <106 μm. Subset B had 25% w/v albumin with a scaffold pore size of 106-150 μm. Subset C had 50% w/v albumin solder with a scaffold pore size <106 μm, while Subset D had a 50% w/v albumin with a scaffold pore size of 106-150 μm. Before depositing the adhesive, the tissue surface was blotted with cotton gauze to remove excess moisture. A strip of adhesive with surface dimensions of 3.0×1.0 mm was then placed over the transection, such that it bridged across the apposed tissue edges, and irradiated with a diode laser operating at a wavelength of 808 nm (Spectra Physics, Mountain View, Calif.). The laser light was coupled into a 660 μm diameter silica fiber bundle and focused onto the adhesive surface with an imaging hand-piece connected at the end of the fiber. Since 808 nm is outside the visible spectrum, the laser included a low-power aiming beam at 632 nm to assist the operator. Surgical outcome was unaffected by the aiming beam due to its low irradiance, as well as the poor absorption of the chromophore at this wavelength. The diode was operated in continuous mode with a spot size at the adhesive surface of approximately 1 mm. An irradiance of 15.9 W/cm$^2$, as measured using a Fieldmaster GS power meter with a LM100 thermopile detector (Coherent Scientific, Santa Clara, Calif.), was delivered to the adhesive, with a scan rate of approximately 0.5 mm/s. Breaking point tensile strength was measured within minutes of solder activation.

Group II: Sclera-to-Sclera Adhesion

Utilizing a 50% w/v BSA solder with 0.5 mg/ml ICG in a PLGA scaffold (106-150 μm pore size) uniform 4.0×3.0 mm samples of human sclera, which had been previously prepared by transecting sclera with a #15 Bard-Parker blade, were joined together (n=20). Two segments were positioned adjacent to each other on parafilm. Scaffolds impregnated with solder were trimmed to a size of 3.0×1.0 mm, placed over the transection, such that they bridged across the apposed scleral tissue edges, and irradiated with a diode laser operating at a wavelength of 808 nm. The same repair procedure used for Group I was applied, with the exception that only the optimal adhesive parameters determined in Group I were tested (set D). Tensile strength was measured within minutes of solder activation.

Group III: Extraocular Rectus Muscle-to-Sclera Adhesion

A 360° conjunctival peritomy was performed on the globes exposing the sites of extraocular muscle attachment. The superior rectus muscle was carefully dissected from the globe using scissors. With the use of sharp dissection, all other attachments to the globe were then removed. The rectus extraocular muscle was re-approximated to the sclera using a pair of forceps such that the end of the muscle was located adjacent to, but not overlying the original site of insertion. Excess moisture was blotted away. A piece of adhesive with surface dimensions of 3.0×1.0 mm was then applied across the top of the tissues in a band-aid-like fashion and irradiated with the 808 nm laser. The point of attachment was thus the superior aspect of the muscle. As with Group II, the same repair procedure used for Group I was applied, with the exception that only the optimal adhesive parameters determined in Group I were tested (set D). Tensile strength was measured within minutes of solder activation.

3.4 Tensile Strength Analysis

Tensile strength analysis of the repairs was performed using a calibrated MTS Material Strength Testing Machine (858 Table Top System, MTS, Eden Prairie, Minn.), interfaced with a computer. The repaired tissue specimens were clamped to the tensiometer by pneumatic grips attached to a 100 N load cell and pulled apart along an axis within the plane of adhesion between the tissue and adhesive, at a rate of 1 gravitational force per second, until the repair failed. Failure was defined as complete separation of the tissue edges. The maximal load in Newton's was recorded at the breaking point. The tissue specimens were kept moist during this procedure to avoid the false elevations of repair strength associated with drying. A two-way analysis of variance (ANOVA) was used to analyze and test for mean differences in tensile strength due to BSA and pore size, as well as testing for eventual interaction between these two factors.

3.5 Results

Group I: Extraocular Rectus Muscle-to-Extraocular Rectus Muscle Adhesion (Table 10)

Rabbit extraocular rectus muscle-to-extraocular rectus muscle scaffold soldering was performed to optimize parameters for more physiologic surgical simulations. Four groups were tested (Table 9) in a two-factor two-level experimental design. This design measured the peak tension carried by the muscle before failing. ANOVA statistical analysis demonstrated that tensile strength was significantly greater at the higher level of BSA concentration (P=0.001) and pore size (P<0.001) without significant interaction between these variables (P=0.793). A 50% w/v BSA mixture with 0.5 mg/ml of ICG and a PLGA scaffold with pore size from 106-150 μm produced the greatest tensile strength (Table 10). This provided a breaking load of 4.2±0.60 N or 88% of inherent tissue strength. Rabbit extraocular muscle had an intrinsic breaking load of 4.8±0.72 N.

Group II: Sclera-to-Sclera Adhesion (Table 11)

Table 11 shows the distribution of tensile strengths of the soldered sclera-to-sclera bonds. The average breaking load for these sutureless reattachments of sclera was 2.9±0.37 N.

Group III: Extraocular Rectus Muscle-to-Sclera Adhesion (Table 12)

Table 12 lists the range of breaking strengths of the resulting repairs of the soldered extraocular rectus muscle-to-sclera adhesions. The mean tensile strength of these sutureless bonds was 3.0±0.36 N.

3.6 Conclusions

In the above reported experiments, a scaffold-enhanced light-activated protein solder was used to replace sutures in ocular tissues commonly joined by suturing. The breaking point of the extraocular rectus muscle-to-sclera bond utilizing our repair technique was beyond that of the actively developed horizontal fixation force measured in vivo in humans and suggests that this procedure may be applicable for eye muscle surgery. The inventors determined a mean active fixation force at 50 degrees extreme gaze of 0.73 N for the medial rectus muscle and 0.58 N for the lateral rectus muscle, with a range of 0.47 N to 1.0 N for all individuals measured, much less than that created by the scaffold-enhanced light-activated protein solder bond.

The scaffold-enhanced light-activated solder described above can be utilized as a suture substitute in select ophthalmic surgical procedures. The use of a scaffold-enhanced light-activated solder also has advantages over other adhesives. For example, the scaffold facilitates fine control over adhesive placement and tissue alignment. It provides an additional reinforcement for tensile strength and can act as a slow-release drug delivery system following surgery. The ability to activate the solder with a specific wavelength of light permits long or large wounds to be closed very quickly and precisely. As well as the potential cost savings in suture products, operating room time may be reduced, especially in a resident teaching situation. Also, the time required to precisely align sutures under a microscope can be minimized. These savings are in addition to the goal of reducing safety risks (such as needle-stick injuries and transfer of communicable diseases) and increasing efficacy of surgery for both the patient and the personnel performing the tasks.

In summary, it has been demonstrated that the immediate tensile strengths achieved with scaffold-enhanced light-activated solders are greater than those physiologically required for strabismus surgery and similar results are anticipated for closure of scleral, corneal and conjunctival incisions as well.

EXAMPLE 4

Composites Containing Albumin Protein and Biodegradable Scaffolds: Part 1—Acute Wound Closure Study in a Rat Model Composite adhesives composed of biodegradable scaffolds impregnated with a biological or synthetic adhesive were investigated for use in wound closure as an alternative to using either one of the adhesives alone. Two different scaffold materials were investigated: (i) a synthetic biodegradable material fabricated from poly(L-lactic-co-glycolic acid) (PLGA); and (ii) a biological material, small intestinal submucosa (SIS), manufactured by Cook BioTech. The biological adhesive was composed of 50%(w/v) bovine serum albumin (BSA) solder and 0.5 mg/ml indocyanine green (ICG) dye mixed in deionized water, and activated with an 808-nm diode laser. The tensile strengths of skin incisions repaired in a rat model were measured acutely, and the time-to-failure was recorded.

The tensile strength of repairs formed using the scaffold-enhanced adhesives were on average, 80% stronger than their non-enhanced counterparts, with an accompanying increase in the time-to-failure of the repairs. These results support the theory that a scaffold material with an irregular surface that bridges the wound provides a stronger, more durable and consistent adhesion, due to the dispersion of the tensile stress forces over the many tiny adhesions provided by the irregular surface, rather than one large continuous adhesive contact. This theory is also supported by several ex vivo experiments demonstrating enhanced tensile strength of irregular versus smooth scaffold surfaces in identical tissue repairs performed on bovine thoracic aorta, liver, spleen, small intestine and lung tissue.

4.1 Preparation of PLGA Scaffolds

Porous synthetic polymer scaffolds were prepared from PLGA, with a lactic:glycolic acid ratio of 85:15, using a solvent-casting and particulate leaching technique. The scaffolds were cast by dissolving 200 mg PLGA (Sigma Chemical Company, St. Louis, Mo.) in 2 mL dichloromethane (Sigma Chemical Company). Sodium chloride (salt particle size: 106-150 μm) with a 70% weight fraction was added to the polymer mix. The polymer solution was then spread to cover the bottom surface of a 60 mm diameter Petri dish and left in a fume hood for 24 hours to allow the dichloromethane to evaporate. The salt was leached out of the polymer scaffolds by immersion in filtered deionized water for 24 hours, to create the porous scaffolds. During this period the water was changed 3 to 4 times. The scaffolds were then air dried and stored at room temperature until required. The scaffolds used for incision repair were cut into rectangular pieces with dimensions of 15±0.5 mm long by 10±0.5 mm wide. Prior to use for tissue repair, all PLGA scaffolds were soaked in 100% ethanol for a period of 5 minutes for sterilization purposes, then rinsed thoroughly with sterile saline.

4.2 Preparation of SIS Scaffolds

SIS is prepared from decellularized porcine submucosa, which essentially contains intact extracellular matrix proteins, of which collagen is the most prevalent. Sheets of SIS, with surface dimensions of 50±10 cm and an average thickness of 100 μm, were provided by Cook BioTech (Lafayette, Ind.). The sheets were cut into rectangular pieces with dimensions of 15±0.5 mm long by 10±0.5 mm wide, and rehydrated in saline for at least 10 minutes prior to being used for tissue repair. Prior to use for tissue repair, all SIS scaffolds were sterilized by soaking in 100% ethanol for a period of 5 minutes, then rinsed thoroughly with sterile saline.

4.3 Experimental Groups

Three experimental groups were investigated. Group I repairs were formed using a PLGA scaffold-enhanced light-activated surgical adhesive. The adhesive was a protein solder mix comprised of 50%(w/v) BSA (Cohn Fraction V, Sigma Chemical Company) and ICG dye (Sigma Chemical Company) at a concentration of 0.5 mg/mL, mixed in deionized water. Group II repairs were formed using the same technique as Group I, however, SIS was used as the scaffold. Group III repairs were formed using the same light-activated adhesive as Groups I and II, without the aid of scaffold enhancement.

4.4 Surgical Procedure

Six Wistar rats, weighing 450±50 g, were anesthetized with a mixture of ketamine and xylazine. Four 15 mm long incisions were then made on the dorsal skin of each rat using a #15 scalpel blade: (1) left rostral parasagital; (2) right rostral parasagital; (3) left caudal parasagital; and (4) right caudal parasagital.

Each of the four incision sites made on the dorsal skin of the animals was randomly assigned to one of the three repair techniques to be investigated. This provided a sample size of eight. The scaffolds used for Group I and II repairs were left to soak for a minimum of two hours in the protein solder mix before use. The thicknesses of the solder-impregnated polymer scaffolds, determined by scanning electron microscopy (Hitachi S-3000N Scanning Electron Microscope, Hitachi Scientific Systems Ltd., Hitachinaka, Japan) and measurement with precision calipers (L.S. Starrett Co., Anthol, Mass.), were in the range of 200 to 205 μm.

For Group I "Solder+PLGA" and Group II "Solder+SIS", the tissue surface was blotted dry with cotton gauze to remove any remaining blood and the light-activated adhesive material was then placed across the incision. For Group III "Solder alone", three drops of solder were spread across the edges of the incision, such that the surface area of coverage was approximately equal to that obtained with the scaffold-enhanced adhesives. All laser-assisted repairs were completed with a diode laser operating at a wavelength of 808-nm (Spectra Physics, Mountain View, Calif.). The laser light was coupled into a 660-μm diameter silica fiber bundle and focused onto the scaffold surface with an imaging hand-piece connected at the end of the fiber. The diode was operated in continuous mode with a spot size of approximately 1 mm at the solder surface. An aiming beam was also incorporated into the system and was delivered through the same fiber as the 808-nm beam. An irradiance of approximately 15.9 W/cm$^2$, measured using a Fieldmaster GS power meter with a LM100 thermopile detector (Coherent Scientific, Santa Clara, Calif.), was delivered to the surface of the solder. The laser beam was scanned across the light-activated adhesive at a rate of 0.5 mm/s, with a total irradiation time of 100±2 seconds.

4.5 Tensile Strength Analysis

Following the surgical procedure, all animals were euthanized with pentobarbital, and the surgical sites were excised. Strength testing was performed immediately following excision of the tissue specimens. The integrity of the resultant repairs were determined by tensile strength measurements performed immediately following the repair procedure using a calibrated MTS Material Strength Testing Machine (858 Table Top System, MTS, Eden Prairie, Minn.). This system was interfaced with a personal computer to collect the data. Each tissue specimen was clamped to the strength-testing machine using a 100N load cell with pneumatic grips. The specimens were pulled apart at a rate of 1 gravitational force/sec until the repair failed. Complete separation of the two pieces of tissue defined failure. The maximum load in Newton's was recorded at the breaking point, as well as the time in seconds to failure. In order to avoid variations in repair strength associated with drying, the tissue specimens were kept moist during the procedure.

4.6 Results

Figure 10:
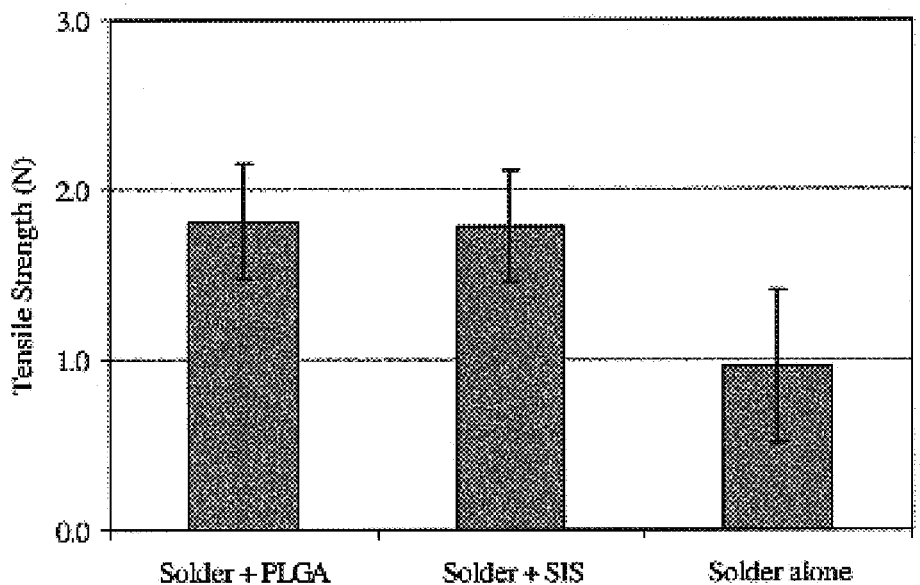
FIG. 10 shows a summary of acute tensile strength data obtained from dorsal skin incisions repaired using three different repair techniques, as described in Example 4. All measurements were made within minutes of completing the surgical procedure.
Figure 11:
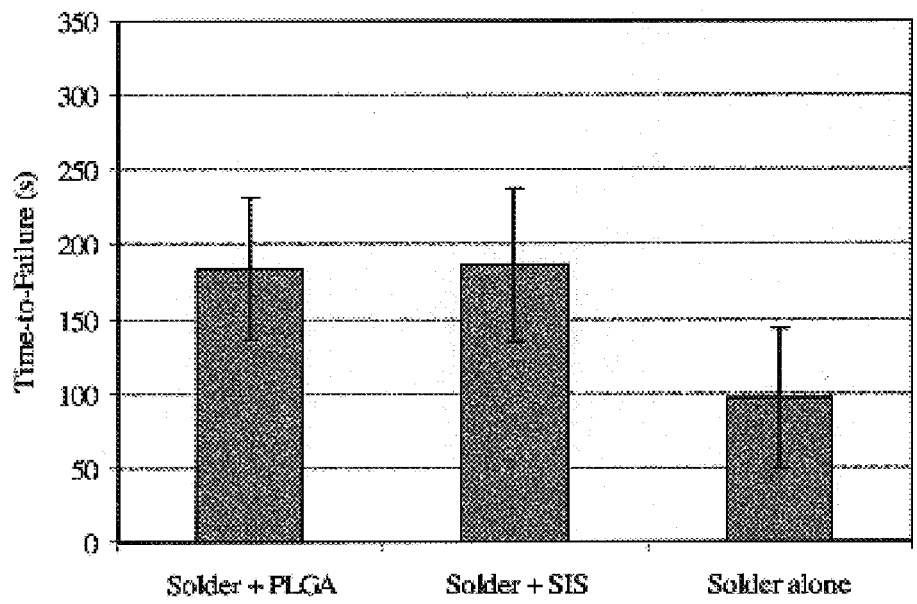
FIG. 11 shows a summary of time-to-failure data obtained from dorsal skin incisions repaired using three different repair techniques, as described in Example 4. All measurements were made within minutes of completing the surgical procedure.

The tensile strength of repairs formed using the three different repair techniques immediately following surgery are shown in FIG. 10. The time-to-failure for each repair technique is shown in FIG. 11. All values are expressed as the mean and standard deviation for a total of eight repairs. The tensile strength of repairs formed using the composite were 150% to 230% of (i.e., 50-130% stronger than) repairs formed by the light-activated adhesive alone, with significantly less variations within each experimental group (average standard deviations of 19% for the scaffold-enhanced biological adhesive (SEBA) versus 47% for adhesive alone). In addition, the time-to-failure curves for repairs formed using the composite showed a longevity not previously seen with the suture or adhesive alone repairs.

EXAMPLE 5

Composites Containing Albumin Protein and Biodegradable Scaffolds: Part II—In Vivo Wound Closure Study in a Rat Model A scaffold and biological adhesive composite was investigated for wound closure as an alternative to sutures or adhesives alone for repair of wounds. Two scaffold materials were investigated: (i) a synthetic biodegradable material fabricated from poly(L-lactic-co-glycolic acid) (PLGA); and (ii) a biologic material, small intestinal submucosa (SIS), manufactured by Cook BioTech. The biological adhesive was composed of 50%(w/v) bovine serum albumin solder (BSA) and 0.5 mg/ml indocyanine green (ICG) dye mixed in deionized water, and activated with an 808-nm diode laser. The tensile strength and time-to-failure of skin incisions repaired in vivo in a rat model were measured at seven days postoperative. Incisions closed by suture or protein solder alone were also tested for comparison. Finally, a histological analysis was conducted to look at variations in wound healing associated with each technique at seven days postoperative.

The tensile strength of repairs formed using the composite were 50% to 65% stronger than repairs formed by suture or adhesive alone, with significantly less variations within each experimental group (average standard deviations of 16% for the composite versus 38% for suture and 32% for adhesive alone). In addition, the time-to-failure curves showed a longevity not previously seen with the suture or adhesive alone repairs. The composite acts to keep the dermis in tight apposition during the critical early phase of wound healing when tissue gaps are bridged by scar and granulation tissue. It has the property of being more flexible than either of the adhesives alone and may allow the apposed edges to move in conjunction with each other as a unit for a longer period of time and over a greater range of stresses than adhesives alone. This permits more rapid healing and the establishment of integrity since the microgaps between the dermis edges are significantly reduced. By the time the scaffolds are sloughed from the wound site, there is greater strength and healing than that produced by adhesive alone or by wounds following suture removal. This hypothesis is supported by the data of this study, as well as, the acute tensile strength data of Example 4.

5.1 Preparation of PLGA Scaffolds

Porous synthetic polymer scaffolds were prepared from PLGA, with a lactic:glycolic acid ratio of 85:15, using a solvent-casting and particulate leaching technique. The scaffolds were cast by dissolving 200 mg PLGA (Sigma Chemical Company, St. Louis, Mo.) in 2 mL dichloromethane (Sigma Chemical Company). Sodium chloride (salt particle size: 106-150 µm) with a 70% weight fraction was added to the polymer mix. The polymer solution was then spread to cover the bottom surface of a 60 mm diameter Petri dish that was cleaned first with dichloromethane, then ethanol, then ultra-filtered deionized water (Fisher Scientific, Pittsburgh, Pa.). The polymer was left in a fume hood for 24 hours to allow the dichloromethane to evaporate. The salt was leached out of the polymer scaffolds by immersion in filtered deionized water for 24 hours, to create the porous scaffolds. During this period the water was changed 3 to 4 times. The scaffolds were then air dried and stored at room temperature until required. The scaffolds used for incision repair were cut into rectangular pieces with dimensions of 15±0.5 mm long by 10±0.5 mm wide. Prior to use for tissue repair, all PLGA scaffolds were soaked in 100% ethanol for a period of 5 minutes for sterilization purposes, then rinsed thoroughly with sterile saline.

5.2 Preparation of SIS Scaffolds

SIS is prepared from decellularized porcine submucosa, which essentially contains intact extracellular matrix proteins, of which collagen is the most prevalent. Sheets of SIS, with surface dimensions of 50×10 cm and an average thickness of 100 µm, were provided by Cook BioTech (Lafayette, Ind.). The sheets were cut into rectangular pieces with dimensions of 15±0.5 mm long by 10±0.5 mm wide, and rehydrated in saline for at least 10 minutes prior to being used for tissue repair. Prior to use for tissue repair, all SIS scaffolds were sterilized by soaking in 100% ethanol for a period of 5 minutes, then rinsed thoroughly with sterile saline.

5.3 Experimental Groups

Four experimental groups were investigated. Group I repairs were formed using a PLGA scaffold-enhanced light-activated surgical adhesive. The adhesive was a protein solder mix comprised of 50% (w/v) BSA (Cohn Fraction V, Sigma Chemical Company) and ICG dye (Sigma Chemical Company) at a concentration of 0.5 mg/mL, mixed in deionized water. Group II repairs were formed using the same technique as Group I, however, SIS was used as the scaffold. Group III repairs were formed using the same light-activated adhesive as Groups I and II, without the aid of scaffold enhancement. Group IV was a control group, with conventional sutures used to close the incisions.

5.4 Surgical Procedure

Eight Wistar rats, weighing 450±50 g, were anesthetized with a mixture of ketamine and xylazine. Four 15 mm long incisions were then made on the dorsal skin of each rat using a #15 scalpel blade: (1) left rostral parasagital; (2) right rostral parasagital; (3) left caudal parasagital; and (4) right caudal parasagital.

Each of the four incision sites made on the dorsal skin of the animals was randomly assigned to one of the four repair techniques to be investigated. This provided a sample size of eight. The scaffolds used for Group I and II repairs were left to soak for a minimum of two hours in the protein solder mix before use. The thicknesses of the solder-impregnated polymer scaffolds, determined by scanning electron microscopy (Hitachi S-3000N Scanning Electron Microscope, Hitachi Scientific Systems Ltd., Hitachinaka, Japan) and measurement with precision calipers (L.S. Starrett Co., Anthol, Mass.), were in the range of 200 to 205 µm.

For Group I "Solder+PLGA" and Group II "Solder+SIS", the tissue surface was blotted dry with cotton gauze to remove any remaining blood and the light-activated adhesive material was then placed across the incision. For Group III "Solder alone", three drops of solder were spread across the edges of the incision, such that the surface area of coverage was approximately equal to that obtained with the scaffold-enhanced adhesives. All laser-assisted repairs were completed with a diode laser operating at a wavelength of 808-nm (Spectra Physics, Mountain View, Calif.). The laser light was coupled into a 660-μm diameter silica fiber bundle and focused onto the scaffold surface with an imaging hand-piece connected at the end of the fiber. The diode was operated in continuous mode with a spot size of approximately 1 mm at the solder surface. An aiming beam was also incorporated into the system and was delivered through the same fiber as the 808-nm beam. An irradiance of approximately 15.9 W/cm$^2$, measured using a Fieldmaster GS power meter with a LM100 thermopile detector (Coherent Scientific, Santa Clara, Calif.), was delivered to the surface of the solder. The laser beam was scanned across the light-activated adhesive at a rate of 0.5 mm/s, with a total irradiation time of 100±2 seconds.

5.5 Surgical Follow-Up

Following the surgical procedure, all animals received a post-operative analgesic dose of buprenorphine. The animals were then observed for a period of seven days, during which, the integrity, swelling, and bruising of the incisions was monitored daily. At the end of this period the animals were euthanized with pentobarbital, and the surgical sites were excised for tensile strength testing.

5.6 Tensile Strength Analysis

The integrity of the resultant repairs were determined by tensile strength measurements performed immediately following excision of the tissue specimens using a calibrated MTS Material Strength Testing Machine (858 Table Top System, MTS, Eden Prairie, Minn.). This system was interfaced with a personal computer to collect the data. Each tissue specimen was clamped to the strength-testing machine using a 100N load cell with pneumatic grips. The specimens were pulled apart at a rate of 1 gravitational force/sec until the repair failed. Complete separation of the two pieces of tissue defined failure. The maximum load in Newton's was recorded at the breaking point, as well as the time in seconds to failure. In order to avoid variations in repair strength associated with drying, the tissue specimens were kept moist during the procedure.

5.7 Results

Figure 12:
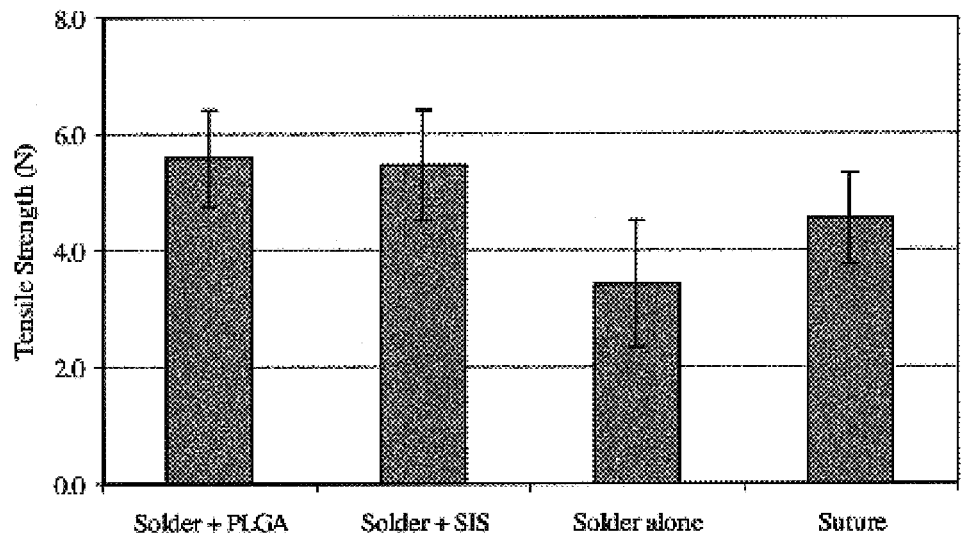
FIG. 12 shows a summary of tensile strength data obtained from dorsal skin incisions repaired using four different repair techniques, as described in Example 5. All measurements were made at seven days postoperative.
Figure 13:
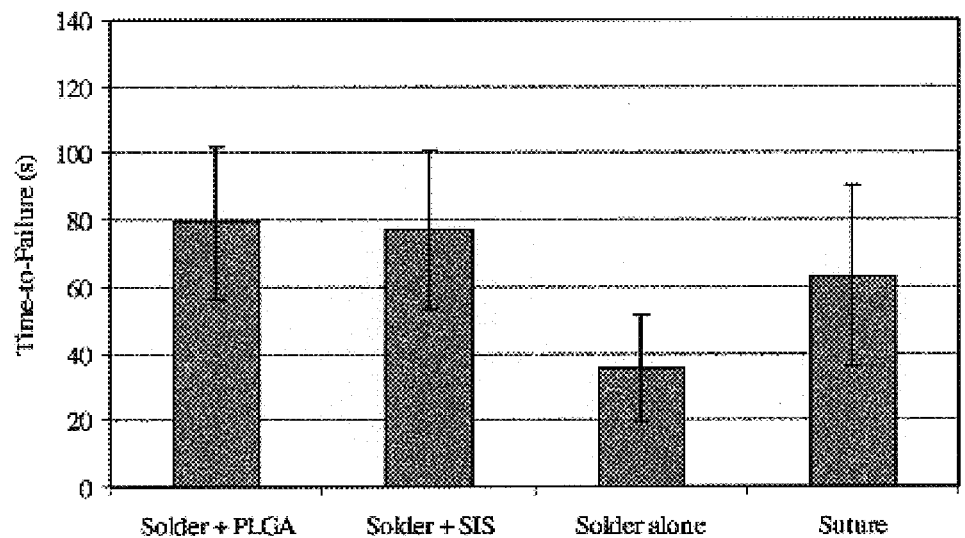
FIG. 13 shows a summary of time-to-failure data obtained from dorsal skin incisions repaired using four different repair techniques, as described in Example 5. All measurements were made at seven days postoperative.

The tensile strength of repairs formed using the four different repair techniques seven days postoperatively are shown in FIG. 12. The time-to-failure for each repair technique is shown in FIG. 13. All values are expressed as the mean and standard deviation for a total of eight repairs.

The tensile strength of repairs formed using the composite were 150% to 165% of (i.e., 50-65% stronger than) repairs formed by the light-activated adhesive alone, with significantly less variations within each experimental group (average standard deviations of 16% for the composite versus 32% for adhesive alone). When compared with suture repair, repairs formed using the light-activated composite were statistically stronger than suture repairs. Here, the tensile strengths of repairs were 120% of (i.e., 20% stronger than) that of suture repairs. The variations observed within each experimental group were also much higher within the suture repair group (average standard deviations of 16% for the composite versus 38% for suture). Finally, the time-to-failure curves for repairs formed using the composite showed a longevity not previously seen with the suture or adhesive alone repairs.

5.8 Conclusions

In the present study the composite is shown to act to keep the dermis in tight apposition throughout the critical early phase of wound healing when tissue gaps are bridged by scar and granulation tissue. The composite thus acts to provide good primary intention healing. On the other hand, secondary intention healing, caused by differential movement of the dermis between the sutures and the contact away from the sutures being constantly stressed, lost and reestablished with the alleviation of stress, always results in a longer time to restoration of wound integrity. Although it is sufficient, it is not optimal and at 7 days histological analysis shows large areas of the wound from the suture repair group (Group IV) that have not healed as well as they would if they were in constant physical apposition and were able to move in concert with externally applied stresses. Similar advantages have previously been observed using the light-activated composite. In this study, histological analysis showed that solder-tissue interaction initially (7 days), and extracellular matrix infiltration of solder later (14 days), provide the basis for improved wound strength, with the scaffold preventing run-away of the fluid solder prior to laser activation.

With appropriate selection of materials and processing parameters, the scaffold can be customized for both the bioadhesive and the intended surgical application. Thus, the resultant scaffold would possess desirable mechanical properties including strength, flexibility, and elasticity, in addition to acting as a vehicle, not only for the delivery of the adhesive, but also for the controlled-release of biologically-active molecules at the site of application. These biological agents may include, hemostatic and thrombogenic agents, antibiotics, anesthetics, various growth factors, enzymes, anti-inflammatories, bacteriostatic or bacteriocidal agents, chemotherapeutic agents, anti-angiogenic agents and vitamins to assist in the therapeutic goal of the procedure. Independent of the choice of materials for the scaffold and adhesive, the end-result is a composite system, which can be used to join tissues together.

In summary, the results of this study indicate that sutureless wound closure using the light-activated composite described here provides increased tensile strength, at 7 days postoperative, when compared with adhesive alone or suture repair techniques. The composite repair technique does not appear to alter the normal wound healing process. Rather, using the light-activated composite, solder-tissue interaction initially, and extracellular matrix infiltration of solder later, appears to provide the basis for improved wound strength.

EXAMPLE 6

Surface Irregularity Improves Mechanical Bonding Properties of a Scaffold-Enhanced Light-Activated Surgical Adhesive An ex vivo study was conducted to determine the effect of scaffold surface irregularity on the tensile strength of repairs formed using our scaffold and light-activated biological adhesive composite.

Two different scaffold materials were investigated: (i) a synthetic biodegradable material fabricated from poly(L-lactic-co-glycolic acid) (PLGA); and (ii) a biological material, small intestinal submucosa (SIS), manufactured by Cook BioTech. The scaffolds were impregnated with a protein solder composed of 50%(w/v) bovine serum albumin (BSA) solder and 0.5 mg/ml indocyanine green (ICG) dye mixed in deionized water and used to repair tissue. The adhesive composite was positioned across the incision site and activated with an 808-nm diode laser operating at an output irradiance of 15.9 W/cm$^2$. Repairs were performed on bovine thoracic aorta, liver, spleen, small intestine and lung tissue specimens, using the smooth and irregular surfaces of the above-described scaffolds applied to the tissue. The tensile strength and time-to-failure of the mechanically stressed repairs were recorded and compared.

The tensile strengths of repairs formed using the irregular surfaces of the scaffolds were consistently higher than the repairs formed using the smooth surfaces of the scaffolds. The largest difference was observed on repairs formed on the aorta and small intestine, where the repairs were, on average, 50% stronger using the irregular versus the smooth scaffold surfaces. In addition, the time-to-failure of repairs formed using the irregular surfaces of the scaffolds were between 150% and 200% of (i.e., 50-100% stronger than) that achieved using the smooth surfaces of the scaffolds.

It has previously been shown that distributing or dispersing the adhesive forces over the increased surface area of the scaffold, either smooth or irregular, produces stronger repairs than albumin solder alone. The increase in the absolute strength and longevity of repairs seen in this new study when the irregular surfaces of the scaffolds are used is thought to be due to the distribution of forces between the many independent micro-adhesions provided by the irregular surfaces.

6.1 Preparation of PLGA and SIS Scaffolds

Porous synthetic polymer scaffolds were prepared from PLGA, with a lactic:glycolic acid ratio of 50:50, using a solvent-casting and particulate leaching technique. The scaffolds were cast by dissolving 200 mg PLGA (Sigma Chemical Company, St. Louis, Mo.) in 2 ml dichloromethane (Sigma Chemical Company). Sodium chloride (salt particle size: 106-150 µm) with a 70% weight fraction was added to the polymer mix. The polymer solution was then spread to cover the bottom surface of a 60 mm diameter Petri dish that was cleaned first with dichloromethane, then ethanol, then ultra-filtered deionized water (Fisher Scientific, Pittsburgh, Pa.). The polymer was left in a fume hood for 24 hours to allow the dichloromethane to evaporate. The salt was leached out of the polymer scaffolds by immersion in filtered deionized water for 24 hours, to create the porous scaffolds. During this period the water was changed 3 to 4 times. The scaffolds were then air-dried and stored at room temperature until used. The PLGA scaffolds were cut into rectangular pieces with dimensions of 10±0.5 mm by 10±0.5 mm. The average thickness of the scaffolds, determined by scanning electron microscopy and measurement with precision calipers, was 150±5 µm. Prior to use for tissue repair, the scaffolds were soaked in phosphate buffered saline for a period of at least 10 minutes.

SIS is prepared from decellularized porcine submucosa, which essentially contains intact extracellular matrix proteins, of which collagen is the most prevalent. Sheets of SIS, with surface dimensions of 50×10 cm and an average thickness of 100 µm, were provided by Cook BioTech (Lafayette, Ind.). The sheets were cut into rectangular pieces with dimensions of 10±0.5 mm by 10±0.5 mm and rehydrated in normal phosphate buffered saline for at least 10 minutes prior to being used for tissue repair.

6.2 Solder Preparation and Impregnation of Scaffolds

Protein solder was prepared from 50% (w/v) BSA (Cohn Fraction V, Sigma Chemical Company, St. Louis, Mo.) and ICG dye (Sigma Chemical Company) at a concentration of 0.5 mg/mL, mixed in deionized water. The solder was stored in light-proof plastic vials at 4° C. until required. Solder remaining after three days was discarded. All scaffolds were immersed in the protein solder mix for a minimum of two hours prior to use.

6.3 Tissue Preparation and LTS Repair Technique

Bovine tissue specimens from the thoracic aorta, liver, spleen, small intestine, and lung were harvested approximately 30 minutes after sacrificing the animals. Specimens were stored in phosphate buffered saline for a maximum of two hours before they were cut to approximate dimensions of 20 mm×10 mm with a thickness of approximately 1.5±0.5 mm.

A full thickness incision was made through each specimen width using a #10 scalpel and the opposing tissue ends were placed together. A strip of our scaffold and light-activated biological adhesive composite was then placed longitudinally over the incision and thermally bonded to the tissue through light activation with an 808 nm diode laser (Spectra Physics, Mountain View, Calif.). The laser light was coupled into a 660 µm diameter silica fiber bundle and focused onto the solder surface with an imaging hand-piece connected at the end of the fiber. The diode was operated in continuous mode with a spot-size of approximately 1 mm at the surface of the scaffold-enhanced adhesive. A low-power 632 nm aiming beam was also incorporated into the system and was delivered through the same fiber as the 808 nm beam. The response of the chromophore at this wavelength is negligible due to the relatively low irradiance of the aiming beam; the outcome of the procedure was not affected by this factor. An irradiance of approximately 15.9 W/cm$^2$, measured using a Fieldmaster GS power meter with a LM100 thermopile detector (Coherent Scientific, Santa Clara, Calif.), was delivered to the surface of the adhesive. The laser beam was scanned across the adhesive surface at a rate of 0.5 mm/s, with a total irradiation time of 100±2 seconds. A total of ten repairs were performed for each set of adhesive parameters and tissue types investigated.

6.4 Scanning Electron Microscopy

Scanning electron microscopy (SEM) was used to examine the surface roughness of the PLGA and SIS scaffolds. Scaffold specimens to be examined by SEM were cut into squares with dimensions of 9.0±0.5 mm by 5.0±0.5 mm. The specimens were then mounted onto 10 mm diameter aluminum specimen stubs (Electron Microscopy Sciences, Ft. Washington, Pa.) using double-sided conductive carbon tape (Electron Microscopy Sciences, Ft. Washington, Pa.), and coated with gold in an argon atmosphere at 2.5 kV and 20 mA for 90 s using an SPI sputter coater (SPI Instruments, West Chester, Pa.). The coating thickness was approximately 30 nm.

SEM analysis was performed with a Hitachi S-3000N Scanning Electron Microscope (Hitachi Scientific Systems Ltd., Hitachinaka, Japan) at 25 kV. Specimens were placed into a custom-built mount and the mount was placed into the stage of the scanning electron microscope for viewing. SEM images were captured using software included with the instrument. In between procedures, the stub-mounted specimens were placed into specimen boxes to protect the surfaces of the specimens.

6.5 Tensile Strength Analysis

The integrity of the resultant repairs was determined by tensile strength measurements performed immediately following the repair procedure using a calibrated MTS Material Strength Testing machine (858 Table Top System, MTS, Eden Prairie, Minn.). This system was interfaced with a personal computer to collect the data. Each tissue specimen was clamped to the strength-testing machine using a 100N load cell with pneumatic grips. The specimens were pulled apart at a rate of 1 gravitational force/sec until the repair failed, which was defined as complete separation of the two pieces of tissue. The maximum load in Newton's was recorded at the breaking point, as well as the time in seconds to failure. In order to avoid variations in repair strength associated with drying, the tissue specimens were kept moist during the procedure. The strengths of incisions repaired with the light-activated protein adhesive alone, and of corresponding native specimens, were tested and used as references.

6.6 Results

Figure 14A:
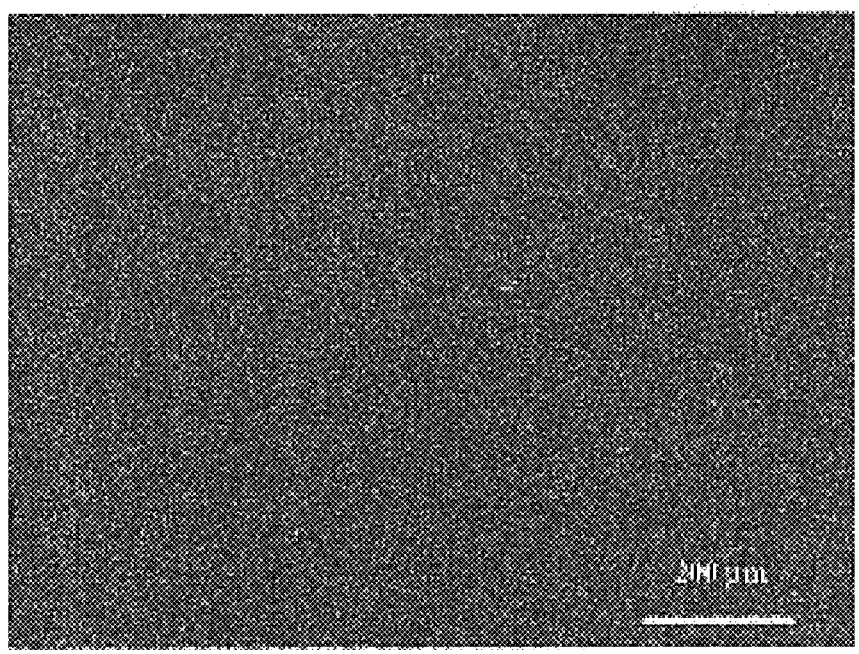
FIGS. 14A and 14B show electron micrographs (magnification: 120×) of the smooth and irregular surfaces of PLGA, respectively.
Figure 14B:
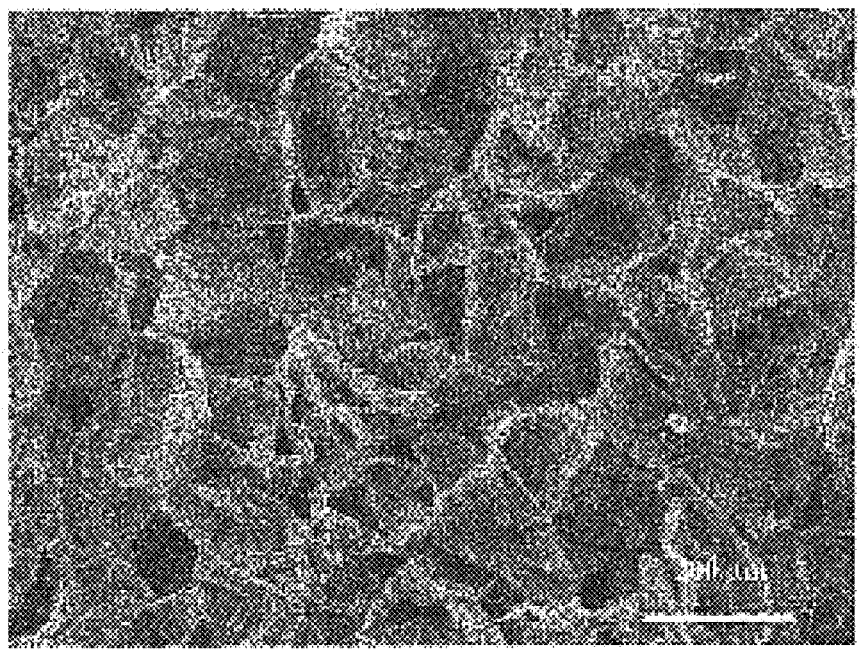
Figure 15A:
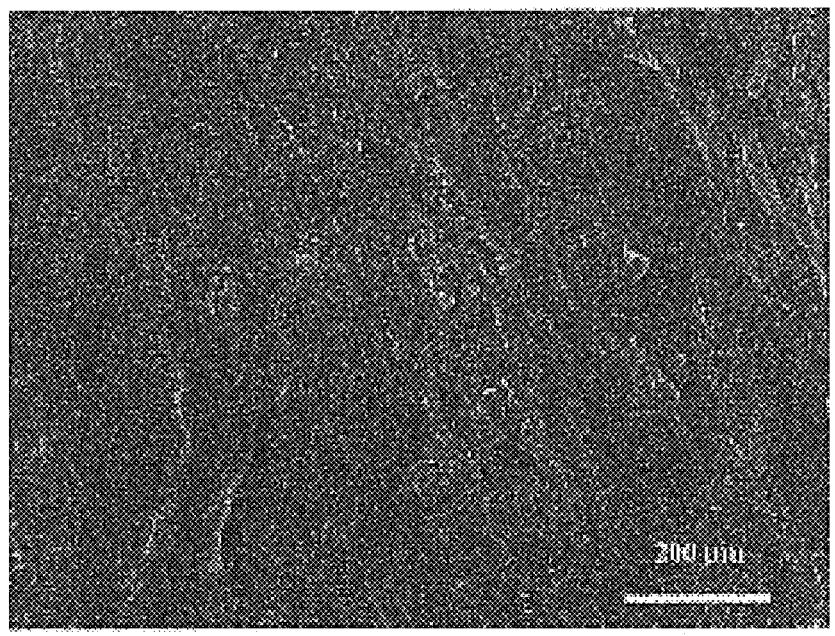
FIGS. 15A and 15B show electron micrographs (magnification: 120×) of the smooth and irregular surfaces of SIS, respectively.
Figure 15B:
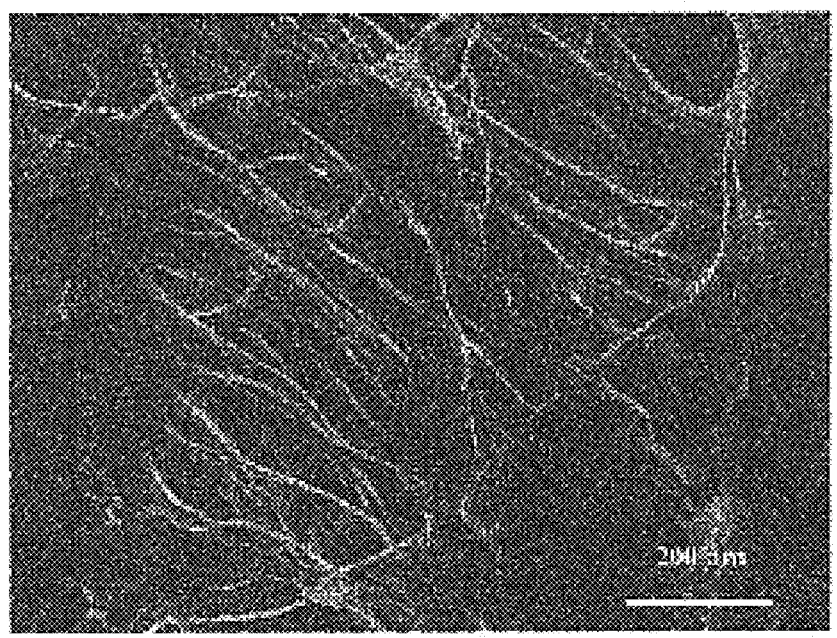

Electron micrographs of both the smooth and irregular surfaces of the PLGA polymer scaffolds are shown in FIGS. 14A and 14B, respectively. Electron micrographs of both the smooth and irregular surfaces of the SIS scaffolds are shown in FIGS. 15A and 15B, respectively. The smooth surface of the PLGA scaffolds represents the side of the scaffold that was cast against the surface of the glass Petri dish. The smooth surface of the SIS scaffolds represents the luminal side of the small intestine.

Figure 16:
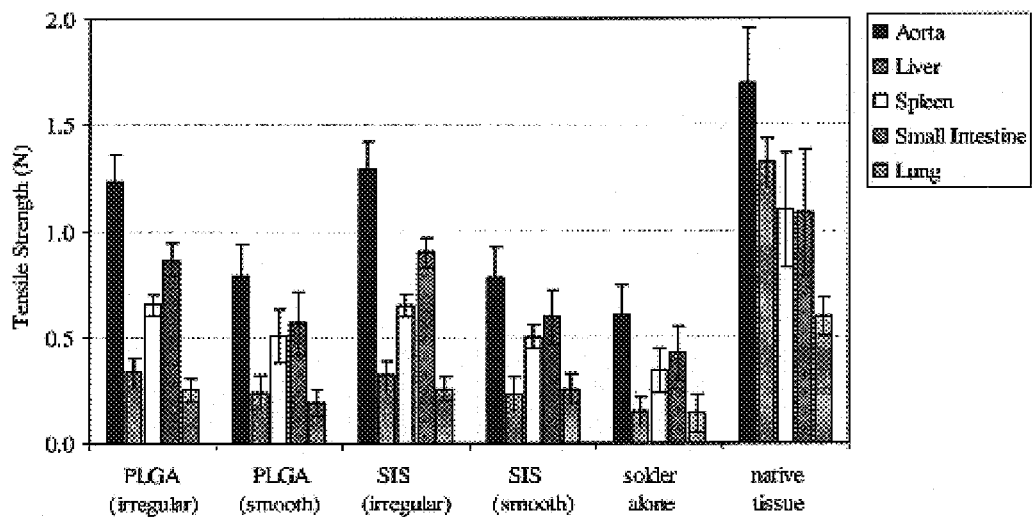
FIG. 16 shows the tensile strength of repairs formed using different scaffold surfaces and a chromophore-doped albumin-based light-activated solder, as described in Example 6. Each bar represents the mean±standard deviation for ten repairs. The tensile strengths of incisions repaired with the light-activated protein adhesive alone and of native tissue are also noted.

The tensile strength of repairs performed on bovine thoracic aorta, liver, spleen, small intestine and lung, by applying either the smooth or the irregular surfaces of the PLGA and SIS scaffolds to the tissue surface are shown in FIG. 16. For the two types of scaffold and light-activated biological adhesive composites investigated, the surface specified corresponds to the side of the scaffold that was placed in contact with the wound tissue. The tensile strength of repairs formed using protein solder alone, and that of native tissue, are also shown in FIG. 16. All data are expressed as the mean and standard deviation for a total of ten repairs. As shown in the graph, the strength of repairs formed using the scaffold-enhanced light-activated adhesives was between 130% and 230% of the results achieved by use of the light-activated protein adhesive alone. In other words, the tensile strength was 30-130% greater using the scaffold-enhanced adhesive.

Figure 17:
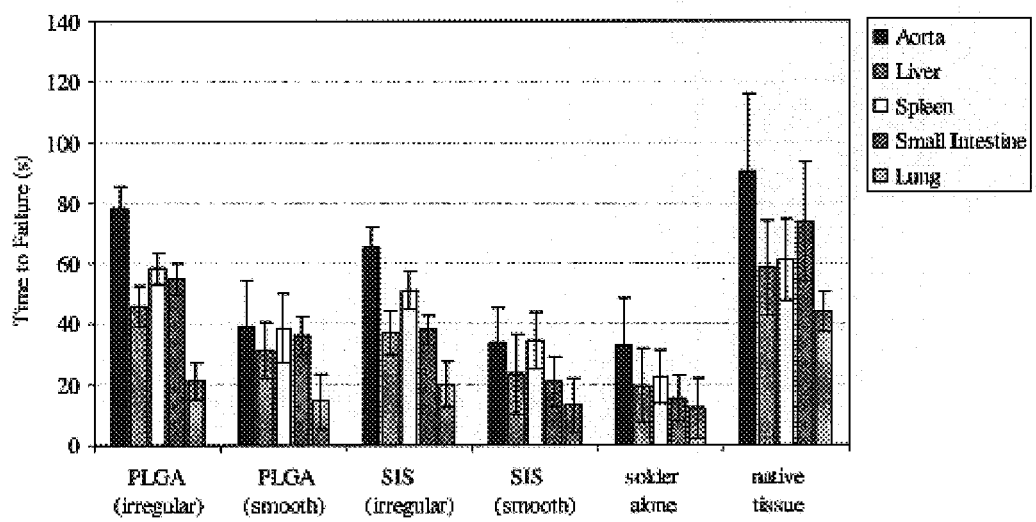
FIG. 17 shows the time-to-failure of repairs formed using different scaffold surfaces and a chromophore-doped albumin-based light-activated solder, as described in Example 6. Each bar represents the mean±standard deviation for ten repairs. The times-to-failure of incisions repaired with the light-activated protein adhesive alone and of native tissue are also noted.
Figure 18:
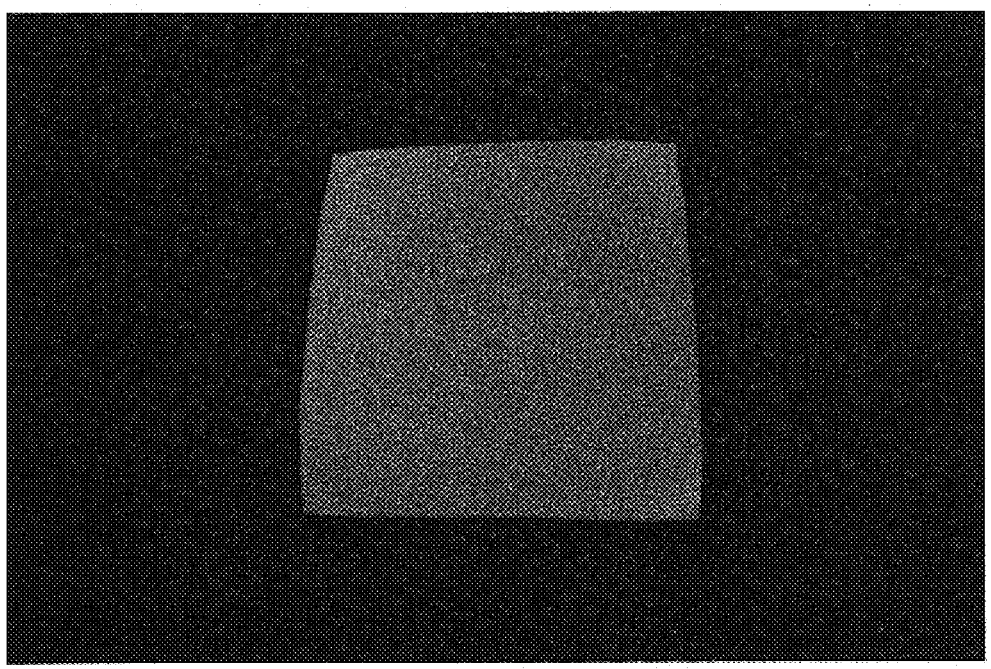
FIG. 18 is a photograph of an embodiment of a scaffold suitable for use in a scaffold-enhanced light-activated biological adhesive, showing a first side of the scaffold.

The time-to-failure for each repair procedure is shown in FIG. 17. All data are expressed as the mean and standard deviation for a total of ten repairs. As shown in the graph, the time-to-failure of repairs formed using the irregular surfaces were between 150% and 200% of (i.e., 50-100% longer than) that achieved using smooth scaffold surfaces.

6.7 Conclusions

The scaffold-enhanced light-activated adhesives examined in this study demonstrated a superior strength profile over those formed using the light-activated adhesive alone, in every tissue type tested. The most notable difference was seen in those tissues that tend to be friable and consequently less amenable to sutures, such as the liver, spleen and lung.

Application of the irregular surface of the scaffold-adhesive composite to the tissue surface resulted in repairs with a tensile strength that was on average 140% of (i.e., 40% greater than) repairs formed using the smooth surface. Thus, the study shows that an irregular surface further increases tensile strength beyond that produced by a scaffold with a smooth surface.

The relative difference in the tensile strengths between the irregular and smooth sides can be explained in the context of (i) differing surface morphologies of the two sides of the scaffold, and (ii) the current understanding of the LTS mechanism.

The solvent casting, particulate-leaching technique used to fabricate the PLGA scaffolds leads to different morphologies forming on each side of the scaffold. The side of the scaffold exposed to the Petri dish is typically smooth, most likely due to the agglomeration of a higher number of salt particles during the casting step. The side of the scaffold exposed to air seems to exhibit a rougher (irregular) surface morphology due to increased diffusion of water, hydrolysis of ester bonds, and subsequent erosion of the surface during the rinsing/evaporation step. SEM analysis confirms that the irregular side of the PLGA scaffolds appears rougher with numerous troughs and valleys on the order of 130±20 μm (FIG. 14b).

The current understanding of the LTS mechanism is that bonding occurs through simultaneous thermal denaturation of BSA and extra-cellular matrix (ECM) proteins of the wound tissue when exposed to laser light. It is hypothesized that more BSA is adsorbed to the irregular side of the scaffold (both PLGA and SIS) due to the increased surface area relative to the smooth side. The increased ligand density of the irregular surface offers the opportunity to form many more 'micro-adhesions' with the integrins of the ECM upon exposure to laser light. The result is increased tensile strength due to the distribution of the shearing forces or breaking forces over a wide area of small independent adhesions. The distribution of breaking/shearing forces provides a plausible explanation for the prolonged time-to-failure behavior of the length-tension curves. For example, in several of these experiments, the tensile strength graphs developed several mini-peaks and valleys as the breaking forces were resisted before ultimately failing at much higher tensions than that of solder alone (or even smooth scaffolds and solder) (results not published).

The scaffold-enhanced light-activated tissue adhesives described in this study could substitute for suture methods of tissue closure in a broad range of surgeries; thereby avoiding the inherent problems and potential complications associated with such mechanical closure techniques, including foreign body reaction and mechanical tissue injury. Other advantages of this scaffold-enhanced adhesive system include reduced operating time and increased precision of tissue adhesion and repair. Additionally, the selection of adhesives with desirable sealant properties would provide an important adjuvant to mechanical methods, such as suture, staple and clip wound closures and tissue appositions. The incorporation of the scaffold as a carrier for the adhesive also permits precise application of the adhesive in the surgical field. This improved ease of clinical use makes the composite useful to many fields of surgery, ranging from neurosurgery and trauma surgery to cosmetic surgery.

In summary, the results of this study indicate that a scaffold-enhanced light-activated adhesive system produces sufficient immediate tensile strength to be effective in many types of surgical tissue repair and wound closure.

EXAMPLE 7

Figure 19:
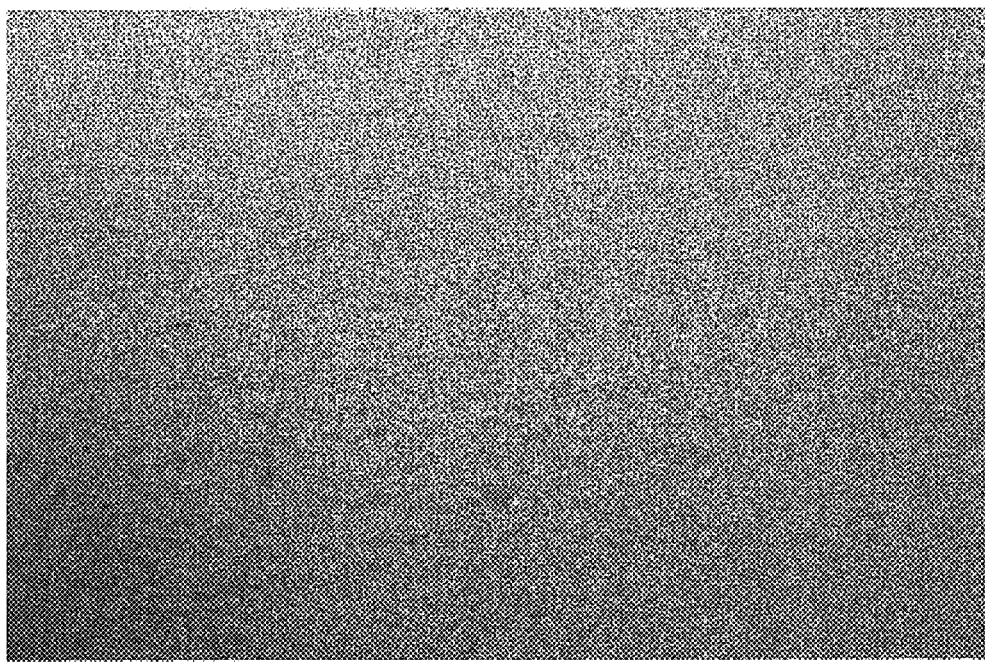
FIG. 19 is a photograph of the scaffold of FIG. 18, showing a close-up view of the first side of the scaffold.
Figure 20:
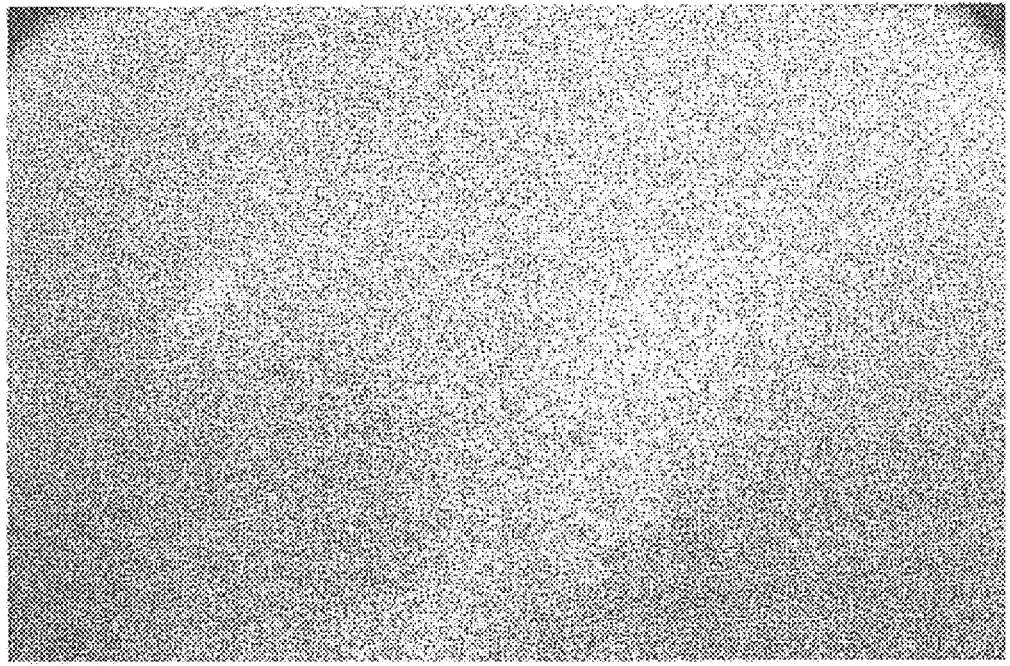
FIG. 20 is a photograph of the scaffold of FIG. 18, showing a close-up view of a second side of the scaffold.
Figure 21:
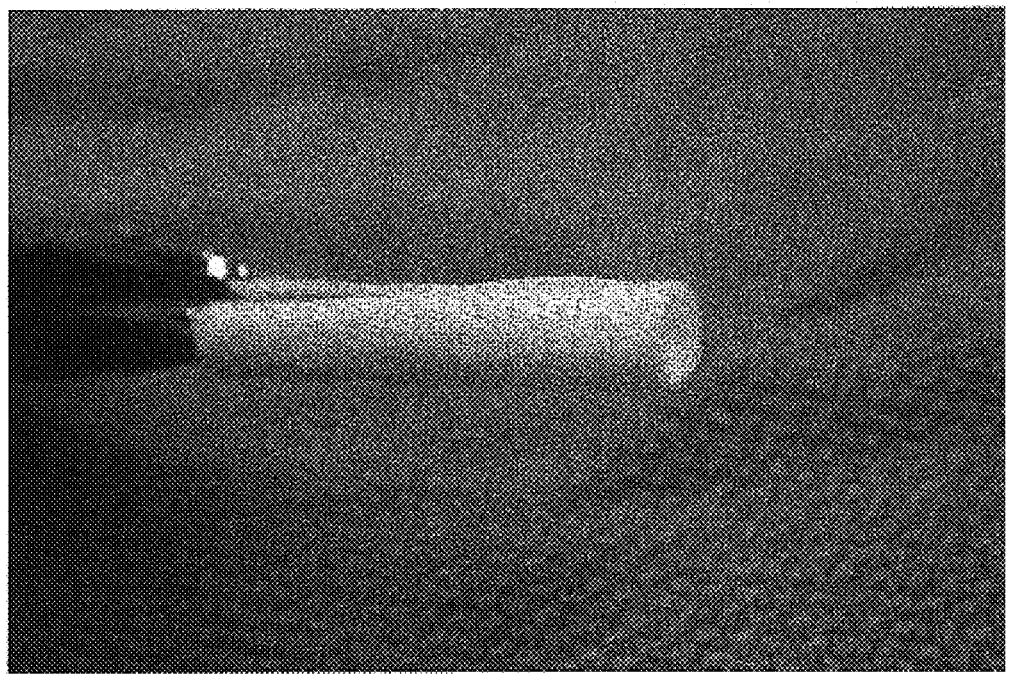
FIG. 21 is a photograph of the scaffold of FIG. 18, showing a first perspective view of the scaffold in a rolled configuration with the first side facing outward.
Figure 22:
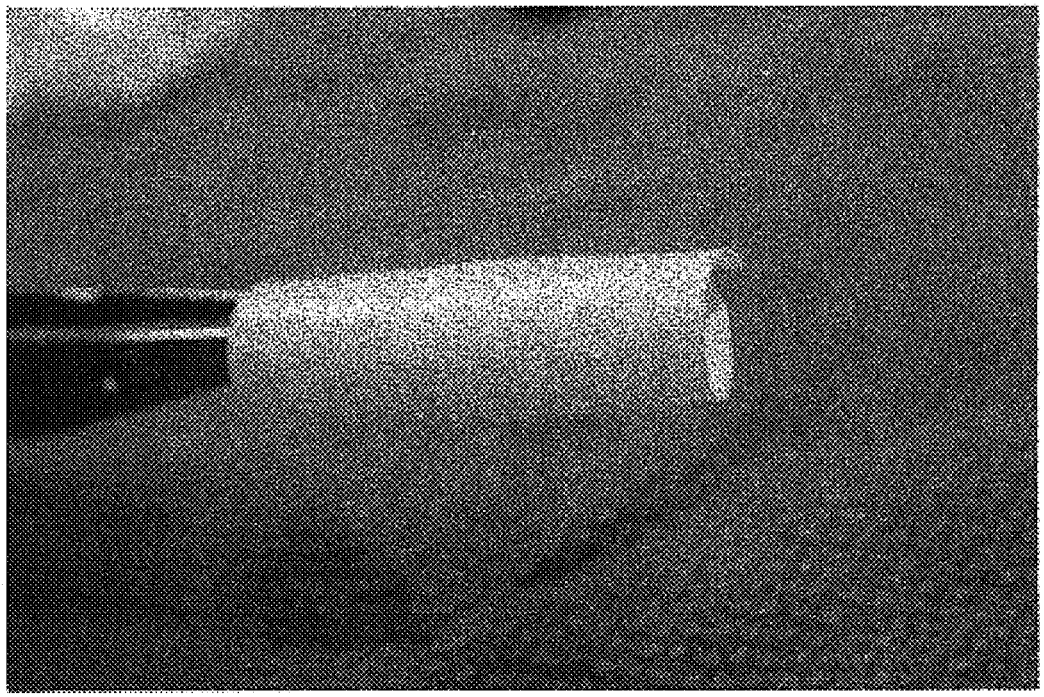
FIG. 22 is a photograph of the scaffold of FIG. 18, showing a second perspective view of the scaffold in a rolled configuration with the second side facing outward.
Figure 23:
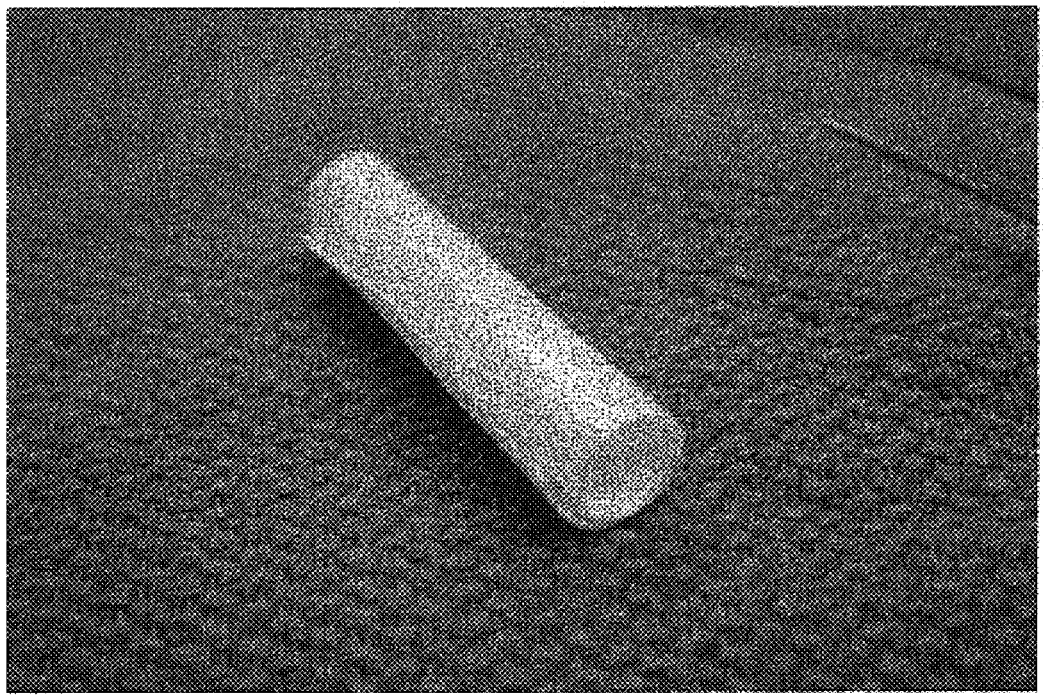
FIG. 23 is a photograph of the scaffold of FIG. 18, showing a third perspective view.
Figure 24:
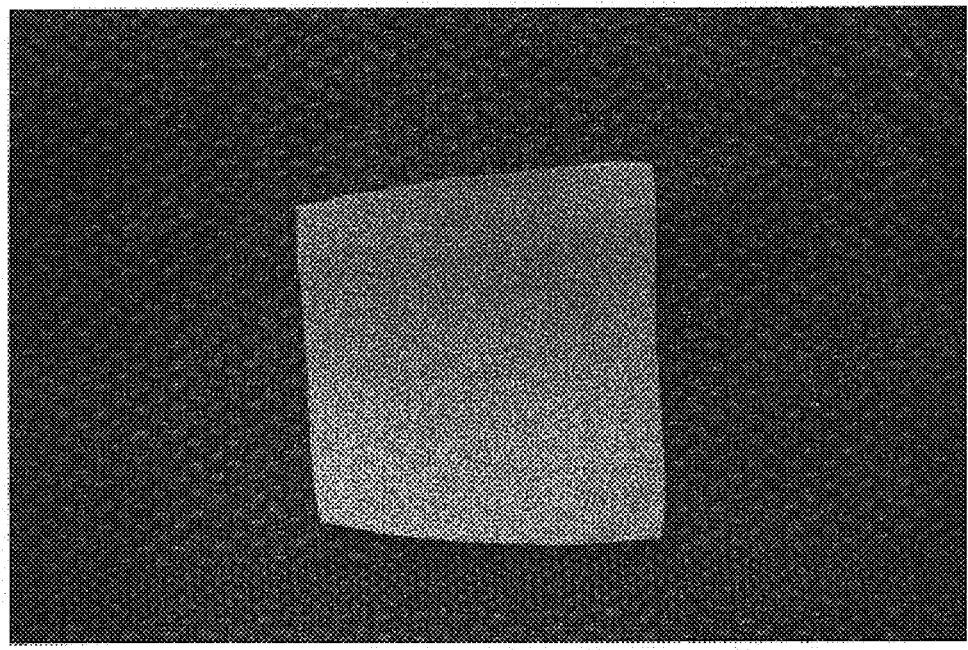
FIG. 24 is a photograph of the scaffold of FIG. 18, showing a fourth perspective view.

Various Views of Embodiment of a Scaffold Suitable for Use in the Scaffold-Enhanced Light-Activated Adhesive FIGS. 18-24 show photographs of various views of one embodiment of a PLGA scaffold suitable for use in the scaffold-enhanced light-activated adhesive discussed above. In the illustrated embodiment, the scaffold has a square shape. However, it is understood that the scaffold may be circular, elliptical, trapezoidal, rectangular, or any other suitable shape. FIG. 19 shows that at least one side of the scaffold may have an irregular surface. FIG. 20 shows another side of the scaffold that has a substantially smooth surface. FIGS. 21-24 show the scaffold may be bent, folded, cuffed, or rolled to adapt to various applications.

As discussed above, the specifications of the composite of the present invention can be tailored to meet the specific requirements of a wide range of clinical applications.

The composite of the present invention may be created by a variety of methods or techniques. For example, a physician or other health care provider may place the scaffold in the desired position for tissue repair, sealing, or adhesion, apply the light-activated adhesive to the scaffold, and then apply light energy. Alternatively, the light-activated adhesive may be applied to the scaffold and then the composite containing both scaffold and adhesive placed in position prior to application of light energy. For instance, the scaffold may be immersed in the light-activated adhesive prior to application to a wound site. As another alternative, the adhesive may be placed at the repair site first and then the scaffold applied. Additional quantities of light-activated adhesive may be applied to the site before or after the scaffold or composite is positioned. It is understood that the terms "placed" and "positioned" include applying the adhesive and/or scaffold on a wound, tissue, or repair site, across edges of a wound or incision, and/or across a juncture between tissue and a biocompatible implant to be joined or adhered.

For purposes of commercial distribution, the inventors have determined that the composite is preferably made by immersing the scaffold material in the light-activated adhesive. Optionally, the composite may be allowed to dry, however, this may not be an ideal form of packaging. The composite can be packaged and distributed with or without a light absorber and/or source of light energy. A selected light absorber is optionally incorporated into the light-activated adhesive, prior to packaging or prior to use.

Although specific illustrated embodiments of the invention have been disclosed, it is understood by those skilled in the art that changes in form and details may be made without departing from the spirit and scope of the invention. The present invention is not limited to the specific details disclosed herein, but is to be defined by the appended claims.

The invention claimed is:

1. A composition suitable for medical and surgical applications, comprising:
   a biologically compatible scaffold material having at least one irregular surface and including one of small intestine submucosa or poly(L-lactic-co-glycolic acid) (PLGA), and
   a biologically compatible light-activated adhesive, the light-activated adhesive including bovine serum albumin and a light absorber selected from at least one of red food coloring, blue food coloring and green food coloring, the light-activated adhesive also being coupled to the scaffold to form a composite, such that when the irregular surface of the composite is applied to biological tissue and the composite is activated by light energy to repair the biological tissue, the composite has a tensile strength of at least about 130% of the tensile strength of the adhesive alone.

2. A composition adaptable to repair biological tissue, comprising:
   a biologically compatible scaffold material, the scaffold material being selected from at least one of poly(glycolic acid), poly(L-lactic-co-glycolic acid), poly(epsilon-caprolactone), poly(ethylene glycol), poly(ortho ester)s, poly(anhydride)s, small intestine submucosa, polymerized collagen, and polymerized elastin,
   a biologically compatible adhesive including bovine serum albumin, and
   a light absorber including at least one of red food coloring, blue food coloring and green food coloring, the light absorber having a concentration of about 200-1000 μL / 13 mL of deionized water.

3. The composition of claim 2, wherein the light absorber is selected to provide a solder/interface temperature of 66±3° C.

4. The composition of claim 2, wherein the light absorber concentration is about 600 μL / 13 mL deionized water.

5. The composition of claim 2, wherein the green food coloring includes blue #1 and yellow #5.

6. The composition of claim 1, wherein the biologically compatible scaffold material has a defined length and includes a plurality of surface irregularities spaced apart along the length of the scaffold material.

7. The composition of claim 6, wherein the plurality of surface irregularities are introduced to the scaffold material by at least one of molding, drilling and punching.

8. The composition of claim 1, wherein the scaffold material is adapted to deliver a biologically active material to a wound when the composite is applied to the wound.

9. The composition of claim 1, further comprising a biologically active material selected from at least one of antibiotics, anesthetics, anti-inflammatories, bacteriostatics, bacteriocidals, chemotherapeutic agents, vitamins, anti-neovascular growth factors, pro-neovascular growth factors, tissue cell growth factors, hemostatic agents and thrombogenic agents.

10. The composition of claim 1, wherein the scaffold material provides reinforcement for wound repair in combination with the light-activated adhesive without any sutures, stapes, clips or other closure devices.

11. The composition of claim 1, wherein the scaffold material is adapted to provide a continuous alignment of opposing portions of biological tissue needing repair.

12. The composition of claim 1, wherein the poly(L-lactic-co-glycolic acid) has an 85:15 lactic:glycolic copolymer ratio.

13. The composition of 12, wherein the biologically compatible adhesive includes 50% w/v bovine serum albumin.

14. The composition of claim 2, wherein the biologically compatible scaffold material comprises poly(L-lactic-co-glycolic acid) having an 85:15 lactic:glycolic copolymer ratio.

15. The composition of claim 14, wherein the biologically compatible adhesive includes 50% w/v bovine serum albumin.

16. The composition of claim 2, wherein the biologically compatible scaffold material has a defined length and includes a plurality of surface irregularities spaced apart along the length of the scaffold material.

17. The composition of claim 16, wherein the plurality of surface irregularities are introduced to the scaffold material by at least one of molding, drilling, and punching.

18. The composition of claim 2, wherein the scaffold material is adapted to deliver a biologically active material to a wound when the composite is applied to the wound.

19. The composition of claim 2, further comprising a biologically active material selected from at least one of antibiotics, anesthetics, anti-inflammatories, bacteriostatics, bacteriocidals, chemotherapeutic agents, vitamins, anti-neovascular growth factors, pro-neovascular growth factors, tissue cell growth factors, hemostatic agents and thrombogenic agents.

20. The composition of claim 2, wherein the scaffold material provides reinforcement for wound repair in combination with the adhesive without any sutures, stapes, clips or other closure devices.

21. The composition of claim 2, wherein the scaffold material is adapted to provide a continuous alignment of opposing portions of biological tissue needing repair.

22. A composition adaptable to repair biological tissue, comprising:
- a biologically compatible scaffold material, the scaffold material being selected from at least one of poly(glycolic acid), poly(L-lactic-co-glycolic acid), poly(epsilon-caprolactone), poly(ethylene glycol), poly(ortho ester)s, poly(anhydride)s, small intestine submucosa, polymerized collagen, and polymerized elastin,
- a biologically compatible light-activated adhesive including bovine serum albumin, the light-activated adhesive including a light absorber selected from at least one of red food coloring, blue food coloring and green food coloring, the light absorber being selected to provide a solder/interface temperature of 66+3° C. and having a concentration of about 200-1000 µL/13 mL of deionized water.

23. The composition of claim 22, wherein the light absorber concentration is about 600 µL/13 mL deionized water.

24. The composition of claim 22, further comprising a biologically active material selected from at least one of antibiotics, anesthetics, anti-inflammatories, bacteriostatics, bacteriocidals, chemotherapeutic agents, vitamins, anti-neovascular growth factors, pro-neovascular growth factors, tissue cell growth factors, hemostatic agents and thrombogenic agents.

25. The composition of claim 22, wherein the biologically compatible scaffold material comprises poly(L-lactic-co-glycolic acid) having an 85:15 lactic:glycolic copolymer ratio.

26. The composition of claim 22, wherein the biologically compatible adhesive includes 50% w/v bovine serum albumin.

* * * * *

UNITED STATES PATENT AND TRADEMARK OFFICE
CERTIFICATE OF CORRECTION

PATENT NO. : 7,501,133 B2  Page 1 of 1
APPLICATION NO. : 10/757818
DATED : March 10, 2009
INVENTOR(S) : Karen M. McNally-Heintzelman et al.

It is certified that error appears in the above-identified patent and that said Letters Patent is hereby corrected as shown below:

Column 32, line 32, replace the term "stapes" with the term --staples--

Column 33, line 3, replace the term "stapes" with the term --staples--

Column 33, line 16, insert the word --and-- after the term "elastin,"

Signed and Sealed this

Second Day of February, 2010

David J. Kappos
*Director of the United States Patent and Trademark Office*